United States Patent
Tun et al.

(10) Patent No.: US 9,464,093 B2
(45) Date of Patent: Oct. 11, 2016

(54) SUBSTITUTED IMIDAZO[4',5':4,5]CYCLOPENTA[1,2-E]PYRROLO[1,2-A]PYRAZINES AND OXAZOLO[4',5':4,5]CYCLOPENTA[1,2-E]PYRROLO[1,2-A]PYRAZINES FOR TREATING BRAIN CANCER

(71) Applicants: Mayo Foundation for Medical Education and Research, Rochester, MN (US); Osaka University, Osaka (JP)

(72) Inventors: Han W. Tun, Jacksonville, FL (US); Takehiko Yoshimitsu, Osaka (JP); Daisuke Shigeoka, Osaka (JP); Takuma Kamon, Osaka (JP); Zhimin Li, Jacksonville, FL (US); Yushi Qiu, Jacksonville, FL (US); Thomas R. Caulfield, Jacksonville, FL (US)

(73) Assignees: Mayo Foundation for Medical Education and Research, Rochester, MN (US); Osaka University, Osaka (JP)

( * ) Notice: Subject to any disclaimer, the term of this patent is extended or adjusted under 35 U.S.C. 154(b) by 0 days.

(21) Appl. No.: 14/434,868

(22) PCT Filed: Oct. 11, 2013

(86) PCT No.: PCT/US2013/064605
§ 371 (c)(1),
(2) Date: Apr. 10, 2015

(87) PCT Pub. No.: WO2014/059314
PCT Pub. Date: Apr. 17, 2014

(65) Prior Publication Data
US 2015/0274742 A1    Oct. 1, 2015

Related U.S. Application Data

(60) Provisional application No. 61/713,399, filed on Oct. 12, 2012, provisional application No. 61/713,974, filed on Oct. 15, 2012.

(51) Int. Cl.
| | |
|---|---|
| A61K 31/4985 | (2006.01) |
| C07D 241/38 | (2006.01) |
| C07D 487/14 | (2006.01) |
| C07D 487/04 | (2006.01) |
| C07D 498/14 | (2006.01) |

(52) U.S. Cl.
CPC ........... C07D 487/14 (2013.01); C07D 487/04 (2013.01); C07D 498/14 (2013.01)

(58) Field of Classification Search
CPC .................. A61K 31/4985; C07D 241/38
USPC ........................................ 514/250; 544/343
See application file for complete search history.

(56) References Cited

U.S. PATENT DOCUMENTS 4,522,811 A    6/1985 Eppstein et al.

FOREIGN PATENT DOCUMENTS

| WO | WO 02/00196 | 1/2002 |
| WO | WO2006055578 A2 | 5/2006 |

OTHER PUBLICATIONS

D'Ambrosio, et al. Helvetica Chimica Acta, 77(7), 1994, 1895-1902.*
Atai et al., "Osteopontin is up-regulated and associated with neutrophil and macrophage infiltration in glioblastoma," *Immunology.*, 132(1):39-48, Epub Aug. 17, 2010.
Berge et al., "Pharmaceutical salts," *J Pharm Sci*, 66(1): Jan. 1-19, 1977.
Blom et al., "Preparative LC-MS purification: improved compound-specific method optimization," *J Comb Chem.*, 6(6):874-883, Epub Sep. 11, 2004.
Brown et al., "Osteopontin expression and distribution in human carcinomas," *Am J Pathol.*, 145(3):610-623, Sep. 1994.
D'Ambrosio et al., "Agelastatin A, a new skeleton cytotoxic alkaloid of the oroidin family. Isolation from the axinellid sponge Agelas dendromorpha of the Coral sea," *Journal of the Chemical Society, Chemical Communications*, (16): 1305-1306, 1993.
D'Ambrosio et al., "The active centres of agelastatin A, a strongly cytotoxic alkaloid of the coral sea axinellid sponge Agelas dendromorpha, as determined by comparative bioassays with semisynthetic derivatives," *Helvetica chimica acta*, 79(3):727-735, 1996.
Denhardt and Chambers, "Overcoming obstacles to metastasis—defenses against host defenses: osteopontin (OPN) as a shield against attack by cytotoxic host cells," *J Cell Biochem.*, 56(1):48-51, Sep. 1994.
Hale et al., "Total synthesis and mechanism of action studies on the antitumor alkaloid, (-)- agelastatin A," *Strategies and tactics in organic synthesis.* vol. 6, Chapt. 11, pp. 352-394, 2005.

(Continued)

*Primary Examiner* — Douglas M Willis
(74) *Attorney, Agent, or Firm* — Fish & Richardson P.C.

(57) ABSTRACT

This document relates to compounds and compositions useful for treating cancers, such as brain and nervous system cancers. For example, such compounds include a compound of Formula I or a pharmaceutically acceptable salt thereof:

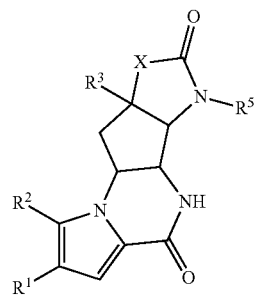

10 Claims, 11 Drawing Sheets

(56) References Cited

OTHER PUBLICATIONS

Hansch et al., "The Correlation of Biological Activity of Plant Growth Regulators and Chloromycetin Derivatives with Hammett Constants and Partition Coefficients," *J. Am. Chem. Soc.*, 85(18):2817-2824, Sep. 20, 1963.

Leo et al., "Partition coefficients and their uses," *Chem Rev*, 71(6): 525-616, 1971.

Li et al., "Pharmacokinetics of Agelastatin A in the central nervous system," *Med. Chem. Commun.*, 3(2): 233-237, print 2012, Epub Nov 1, 2011.

Lipinski et al., "Experimental and computational approaches to estimate solubility and permeability in drug discovery and development settings," *Adv Drug Del Rev.*, 23(1-3): 3-25, Jan. 15, 1997.

Mason et al., "Agelastatin A: a novel inhibitor of osteopontin-mediated adhesion, invasion, and colony formation," *Mol Cancer Ther.*, 7(3):548-558, Mar. 2008.

Mills,"ChemDraw Ultra 10.0 CambridgeSoft, 100 CambridgePark Drive, Cambridge, MA 02140," www.cambridgesoft.com. Commercial Price: 1910fordownload, 2150 for CD-ROM; Academic Price: 710fordownload, 800 for CD-ROM. *J. Am. Chem. Soc.*, 128(41):13649-13650, 2006.

Pettit et al., "Antineoplastic agents 470. Absolute configuration of the marine sponge bromopyrrole agelastatin A," *Oncol Res.*, 15(1):11-20, 2005.

Pétursson et al., "Protecting Groups in Carbohydrate Chemistry," *J. Chem. Educ.*, 74(11): 1297-1303, Nov. 1997.

Schmid et al., "General atomic and molecular electronic structure system," *J. Comput. Chem.*, 14(11): 1347-1363, Nov. 1993

Senger et al., "Elevated expression of secreted phosphoprotein I (osteopontin, 2ar) as a consequence of neoplastic transformation," *Anticancer Res*, 1989, 9(5): 1291-1299, Sep.-Oct. 1989.

Toy et al., "Correliation Between Osteopontin Protein Expression and Histological Grade of Astrocytomas," *Pathology & Oncology Research*, 15(2):203-207, Jun. 2009.

Tun and McKinney, "Differential gene expression of central nervous system lymphoma," *Blood*, 113(1): 267-268, Jan. 1, 2009.

Tun et al., "Pathway analysis of primary central nervous system lymphoma," *Blood.*, 111(6):3200-3210, Epub Jan. 9, 2008.

Yoshimitsu et al., "Total synthesis of the beta-catenin inhibitor, (-)-agelastatin A: a second-generation approach based on radical aminobromination," *Org Lett.*, 11(15):3402-3405, Aug. 6, 2009.

Domostoj et al., "New total synthesis of the marine antitumor alkaloid (-)-agelastatin A," *Org Lett.*, 6(15):2615-2618, Jul. 22, 2004.

Feldman et al., "Alkynyliodonium salts in organic synthesis. Development of a unified strategy for the syntheses of (-)- agelastatin A and (-)-agelastatin B," *J Org Chem.*, 67(20):7096-7109, Oct. 4, 2002.

Li et al., "An integrated approach to the discovery of potent agelastatin A analogues for brain tumors: chemical synthesis and biological, physicochemical and CNS pharmacokinetic analyses," MedChemComm., 4(7):1093-1098, 2013.

Movassaghi et al., "Total synthesis of all (-)-Agelastatin alkaloids," *Chem Sci.*, 1:561-566, Jan. 1, 2010.

Yoshimitsu et al., "Total synthesis of (-)-agelastatin A," *Org Lett.*, 10(23):5457-5460, Dec. 4, 2008.

International Search Report and Written Opinion for PCT/US2013/064605, mailed Feb. 20, 2014, 7 pages.

International Preliminary Report on Patentability for PCT/US20131064605, mailed Apr. 23, 2015, 12 pages.

European Search Report for Application No. 13845901, dated Feb. 15, 2016, 5 pages.

* cited by examiner

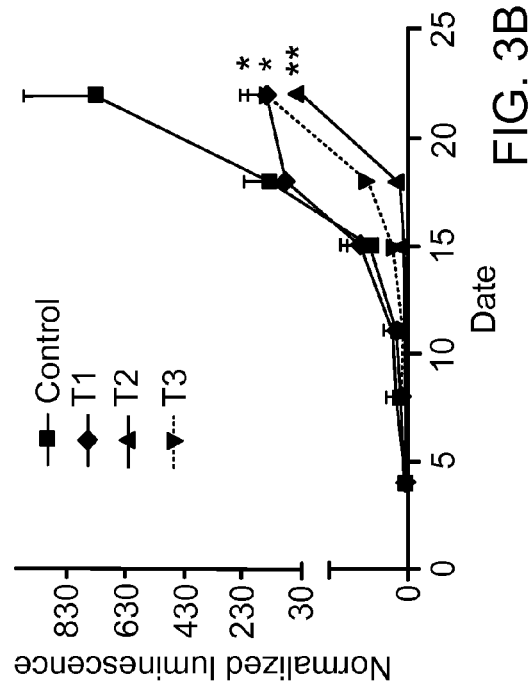
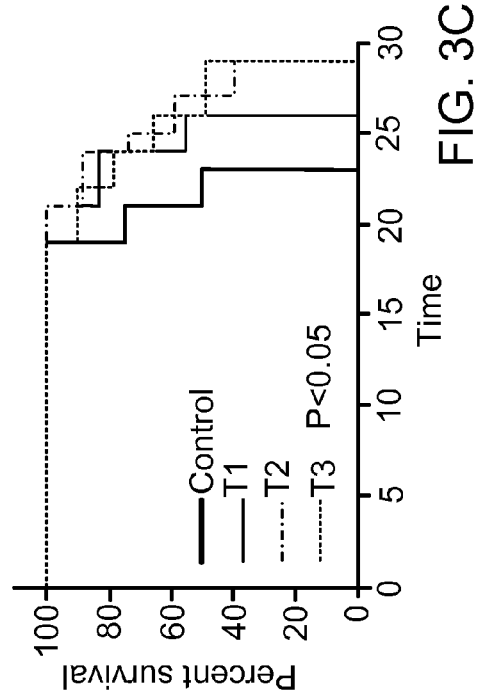
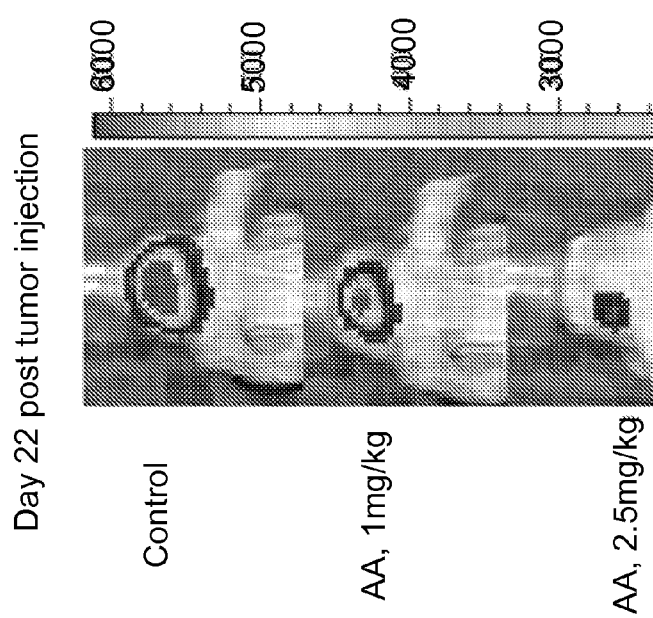
FIG. 3A
FIG. 3B
FIG. 3C

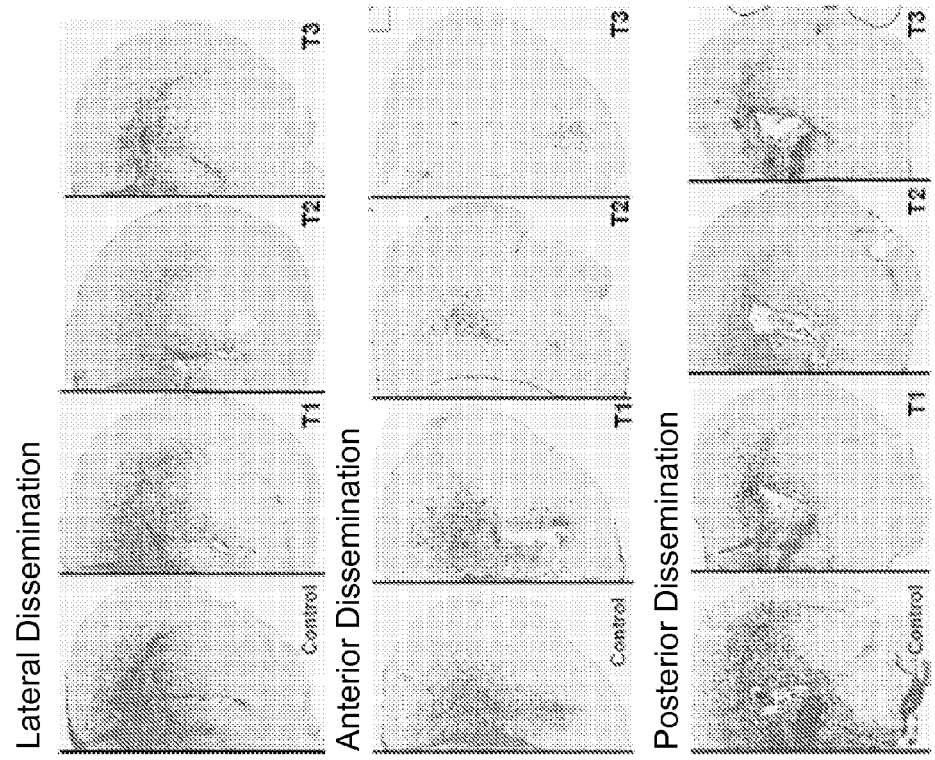
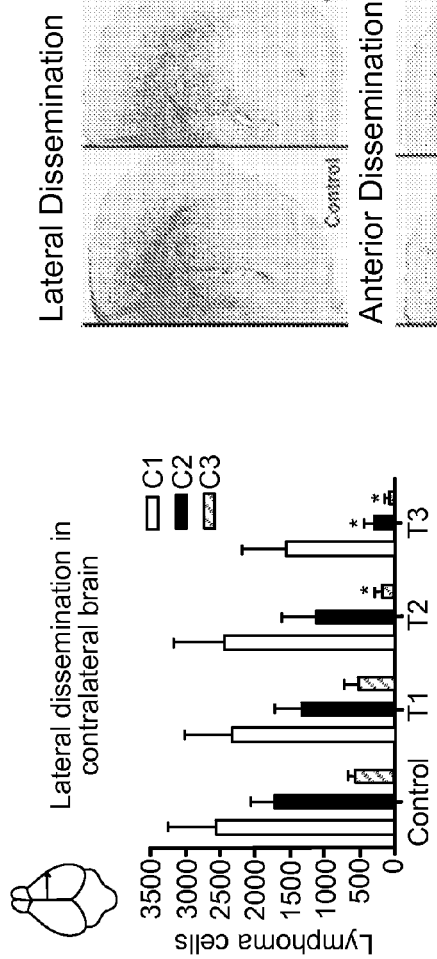
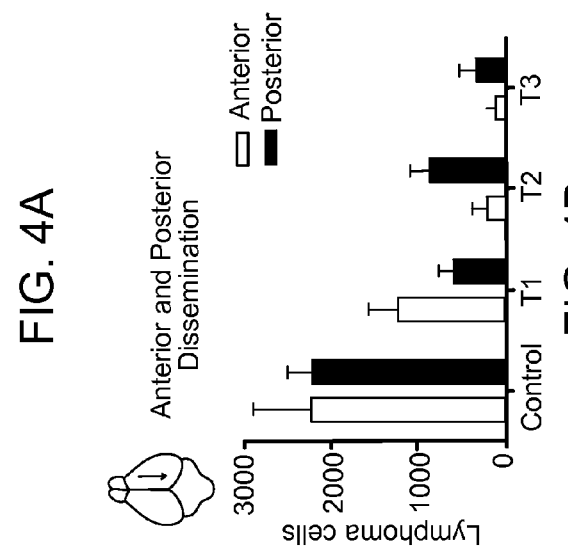
FIG. 4A
FIG. 4B
FIG. 4C

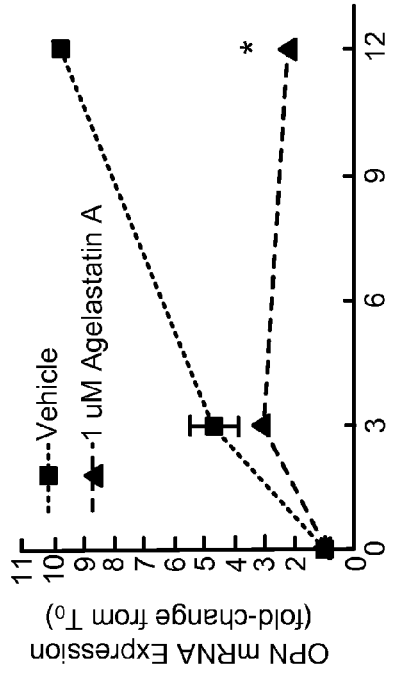
FIG. 5A
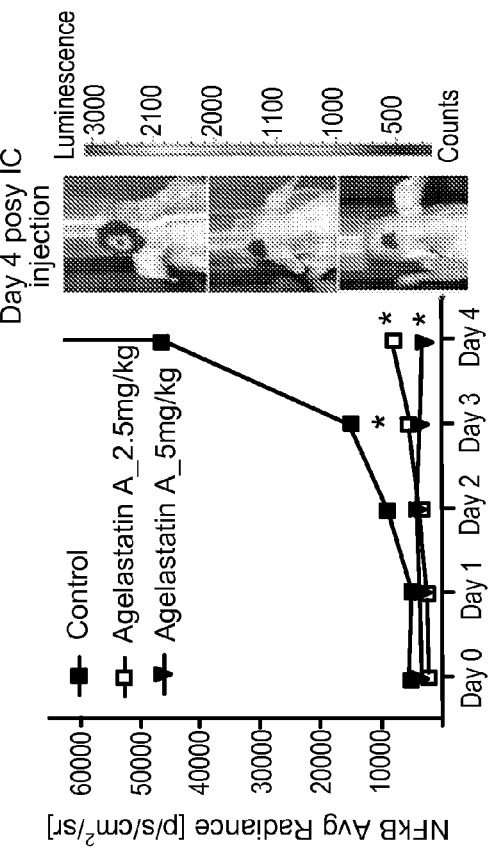
FIG. 5B
FIG. 5D
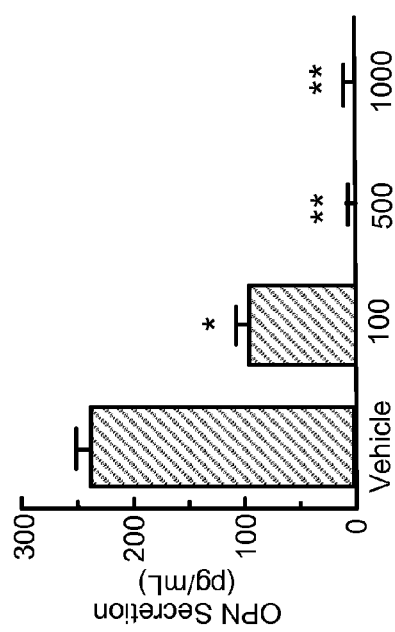
FIG. 5C

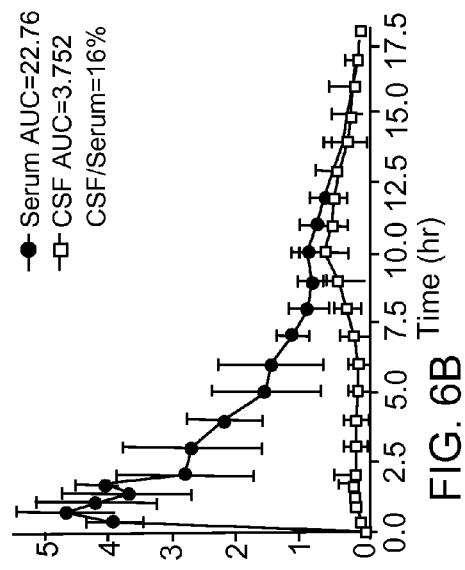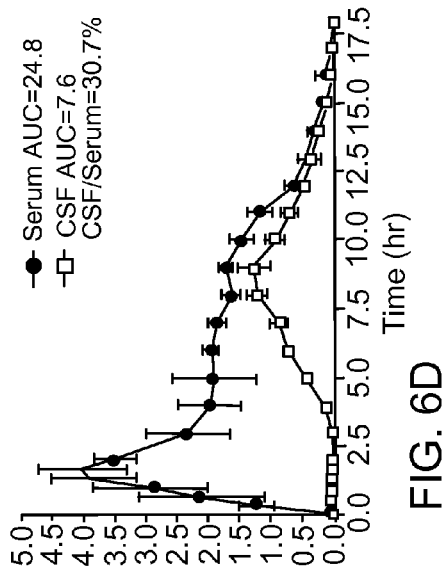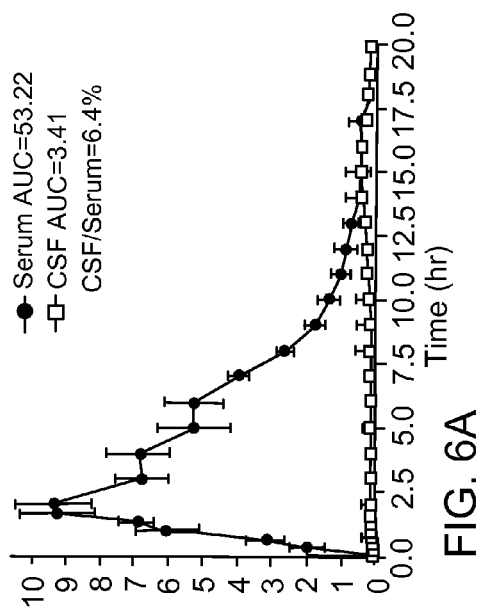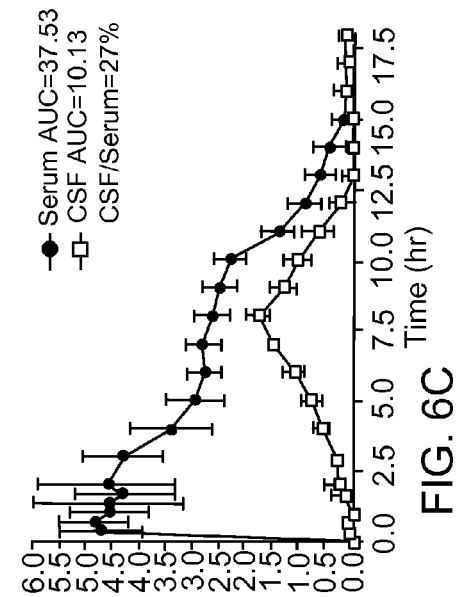

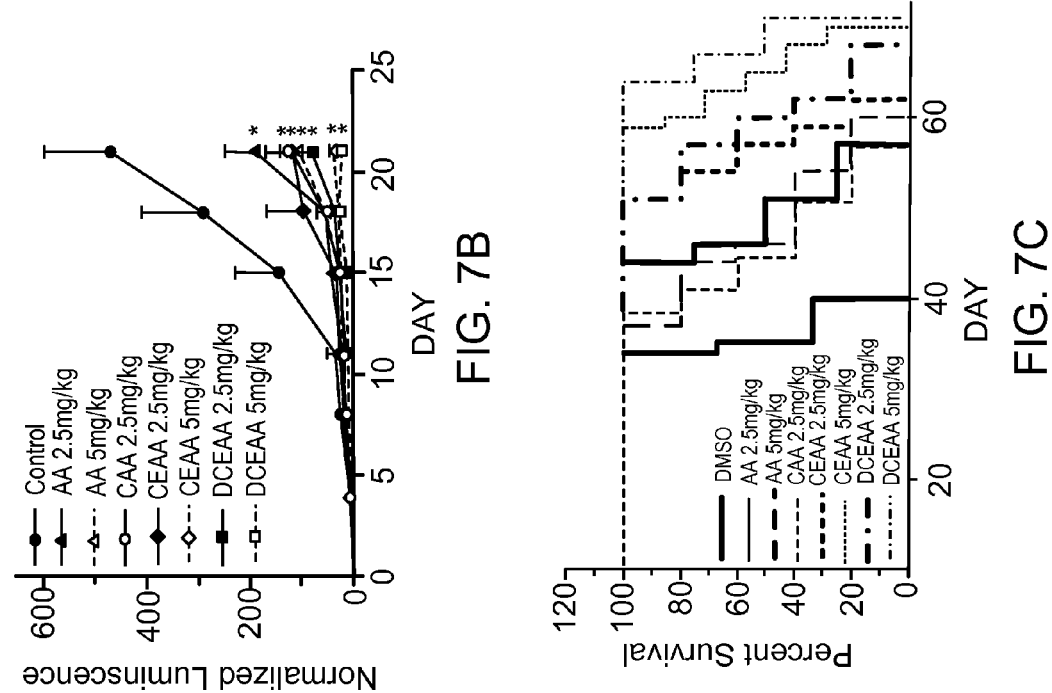
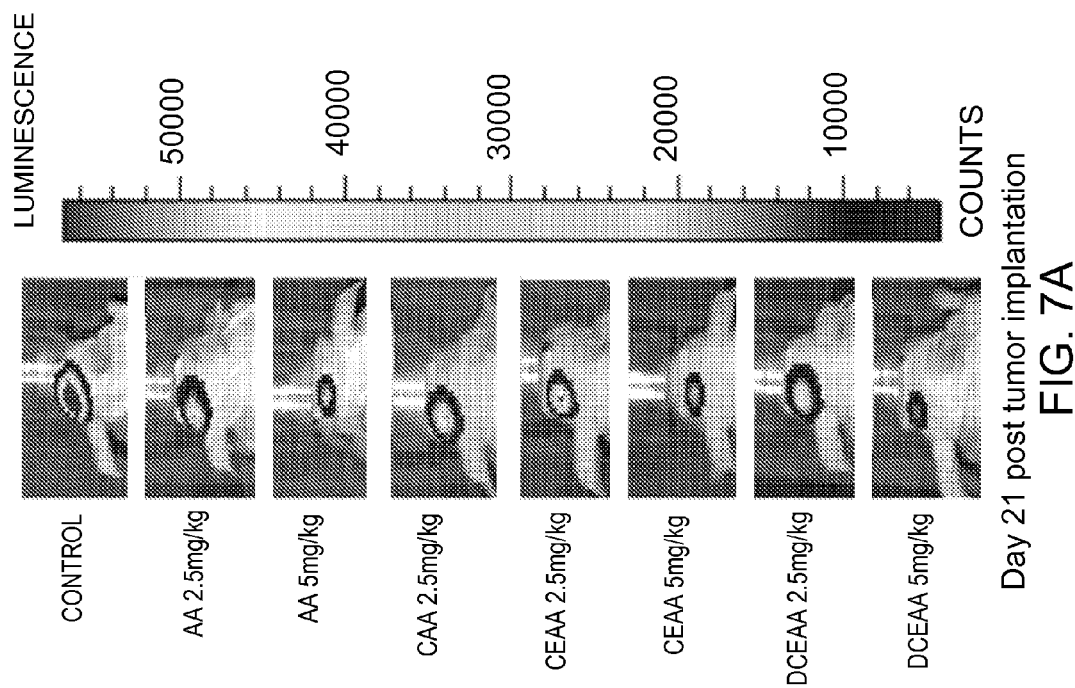
FIG. 7A
FIG. 7B
FIG. 7C

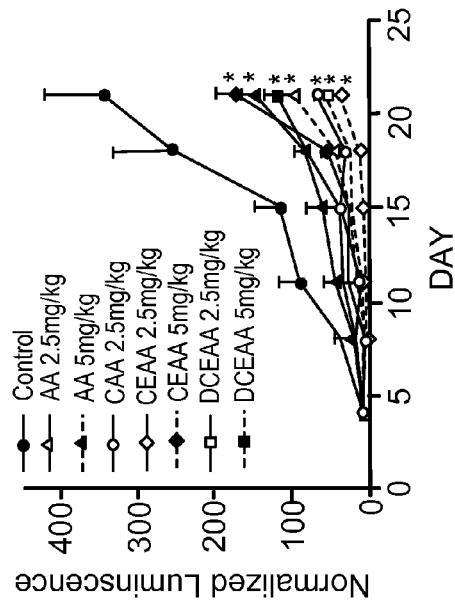
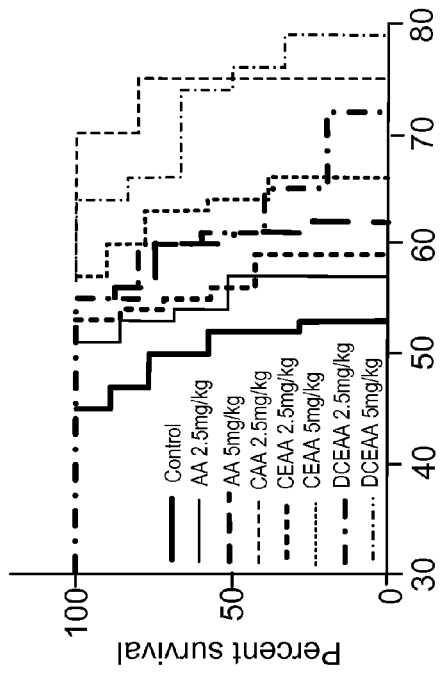
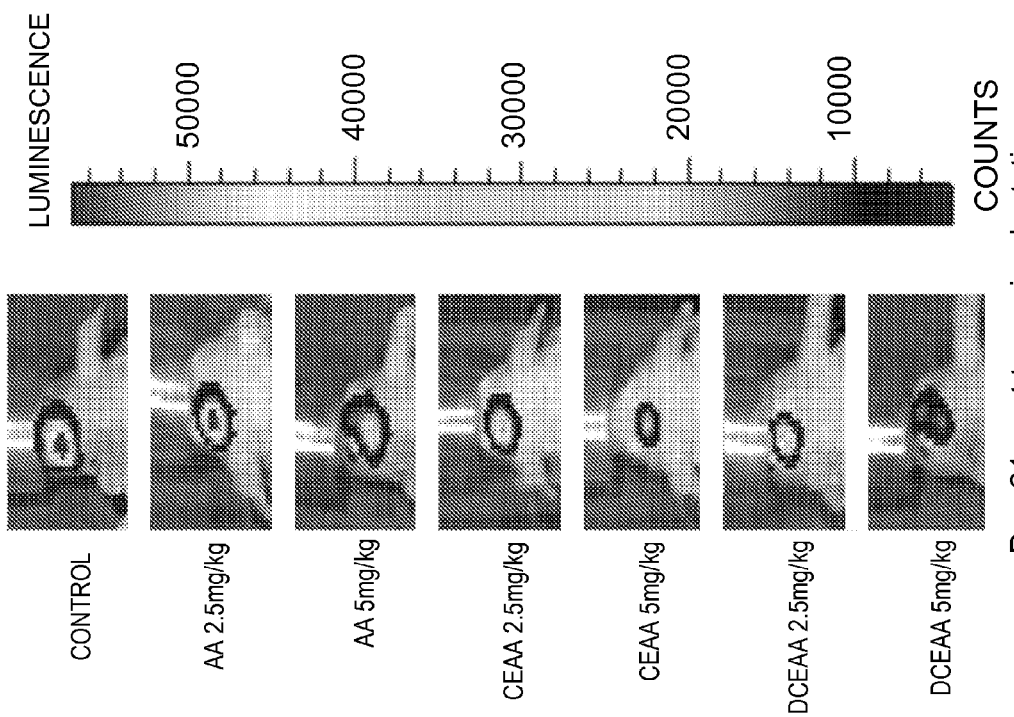
FIG. 8A
FIG. 8B
FIG. 8C

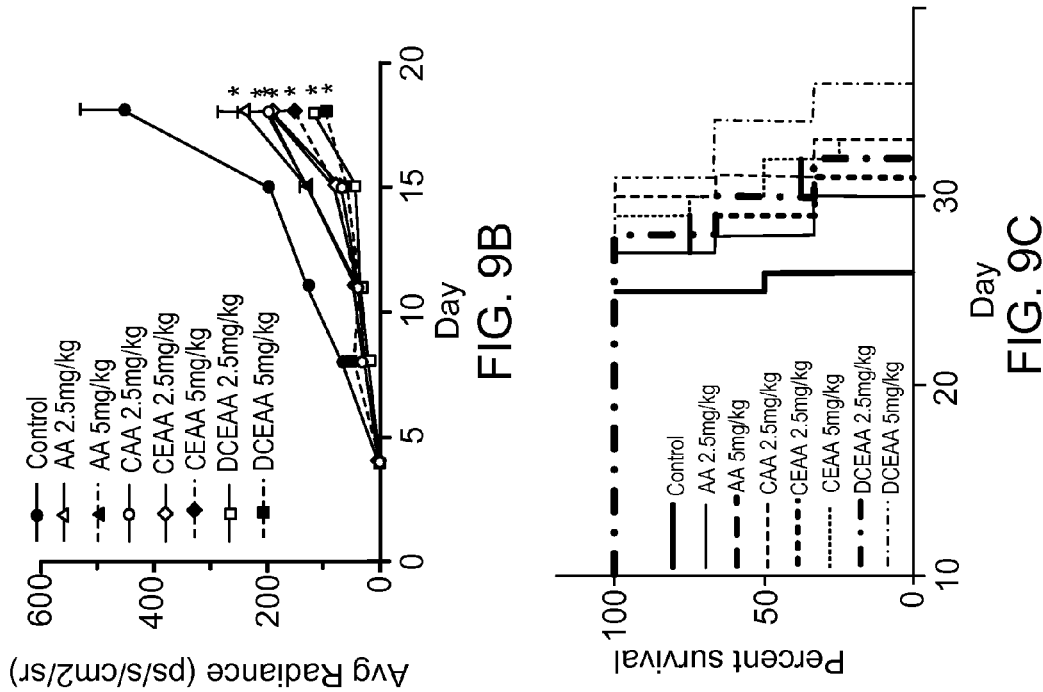
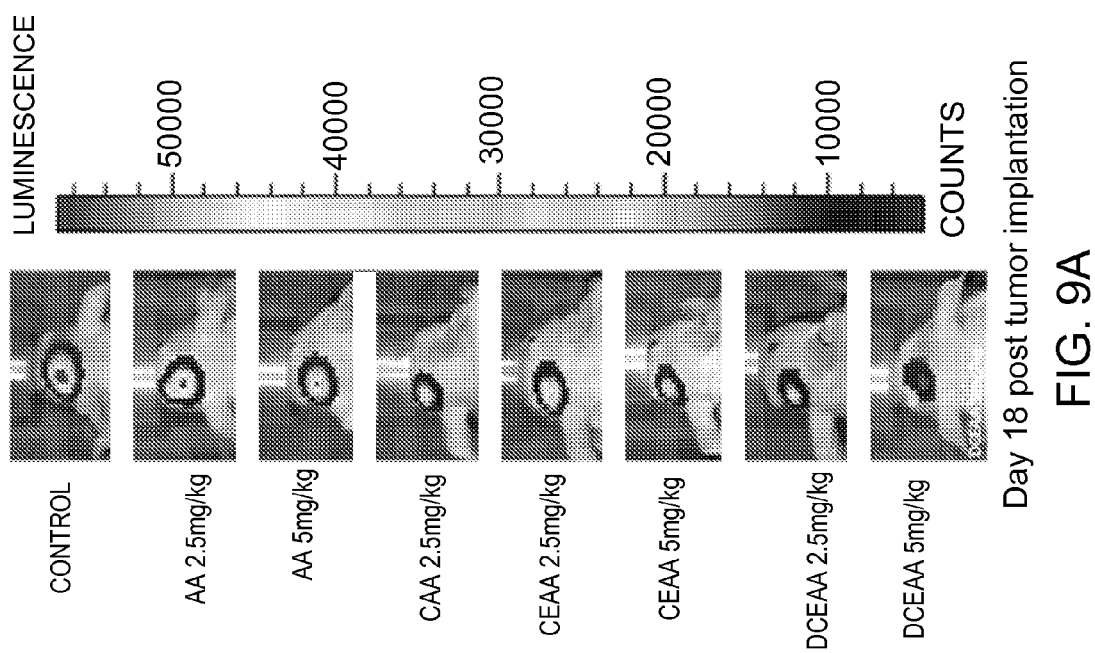
FIG. 9A
FIG. 9B
FIG. 9C

SUBSTITUTED IMIDAZO[4',5':4,5]CYCLOPENTA[1,2-E]PYRROLO[1,2-A]PYRAZINES AND OXAZOLO[4',5':4,5]CYCLOPENTA[1,2-E]PYRROLO[1,2-A]PYRAZINES FOR TREATING BRAIN CANCER

CROSS-REFERENCE TO RELATED APPLICATIONS

This application is a National Stage application under 35 U.S.C. 371 of International Application No. PCT/US2013/064605, having and International Filing Date of Oct. 11, 2013, which claims priority to U.S. Provisional Application Ser. No. 61/713,399, filed on Oct. 12, 2012, and U.S. Provisional Application Ser. No. 61/713,974, filed on Oct. 15, 2012. The disclosures of the prior applications are considered part of (and are incorporated by reference in) the disclosure of this application.

TECHNICAL FIELD

This document relates to compounds and compositions useful for treating cancers, including brain and nervous system cancers.

BACKGROUND

Agelastatin A is an oroidin alkaloid extracted from an axinellid sponge, Agelas dendromorpha. It has anti-neoplastic activities against multiple cancers including breast cancer, lung cancer, colon cancer, head and neck cancer, and bladder cancer (see, e.g., M. D'Ambrosio et al. *J Chem Soc Chem Commun*, 1993, 1305; M. D'Ambrosio et al. *Helv. Chim. Acta*, 1996, 79, 727-735; and M. D'Ambrosio et al. *Helv. Chim. Acta*, 1994, 79, 727-735). It has been shown to be 1.5 to 16 times more potent than Cisplatin (G. R. Pettit et al. *Oncol Res*, 2005, 15, 11-20). Recently it was shown that AA has anti-osteopontin (OPN) activity (K. Mason et al. *Mol Cancer Ther*, 2008, 7, 548-558).

OPN plays an important role in cancer biology and mediates cell proliferation, invasion, metastasis, and angiogenesis. High expression of OPN is found in primary brain tumors including primary CNS lymphoma (PCNSL) and glioblastoma multiforme (GBM). As such, OPN is a valid molecular target for therapeutic development for these aggressive brain tumors.

Current treatments for brain tumors such as PCNSL, GBM, and metastatic breast cancer of the brain are not very effective and carry significant toxicities. Therapeutic agents with better efficacy and toxicity profile are urgently needed.

SUMMARY

Provided herein is a compound of formula I:

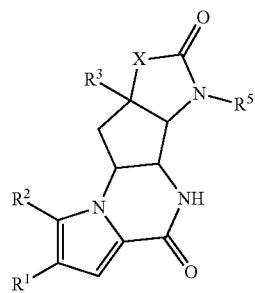

or a pharmaceutically acceptable salt thereof, wherein:

X is O or $NR^4$;

$R^1$ and $R^2$ are independently selected from the group consisting of: H, F, Cl, Br, I, substituted or unsubstituted $C_{1-6}$ alkyl, substituted or unsubstituted cycloalkyl, substituted or unsubstituted aryl, substituted or unsubstituted heterocycloalkyl, and substituted or unsubstituted heteroaryl;

$R^3$ is selected from the group consisting of: H, OH, and $O(C_{1-6}$ alkyl);

$R^4$ and $R^5$ are independently selected from the group consisting of: H and substituted or unsubstituted $C_{1-6}$ alkyl; and wherein if $R^1$ is H, $R^2$ is Br, $R^3$ is OH, and $R^5$ is H, then $R^4$ is not $CH_3$; if $R^1$ is H, $R^2$ is H, $R^3$ is OH, and $R^5$ is H, then $R^4$ is not $CH_3$; and if $R^1$ is H, $R^2$ is H, $R^3$ is H, and $R^5$ is H, then X is not O.

In some embodiments, $R^1$ and $R^2$ are independently selected from H and Cl. In some embodiments, X is $NR^4$. For example, $R^4$ can be a $C_{1-6}$ alkyl such as ethyl. In some embodiments, $R^3$ is OH.

Non-limiting examples of a compound of formula (I) include:

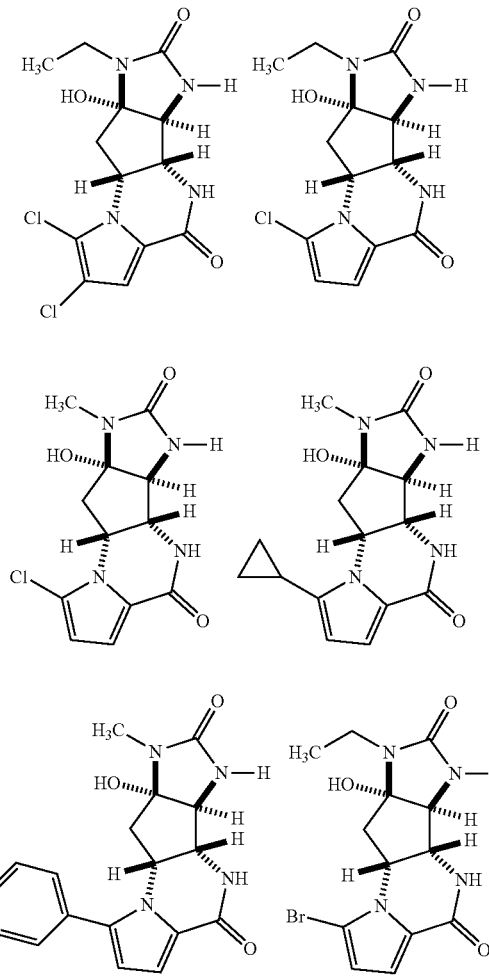

-continued

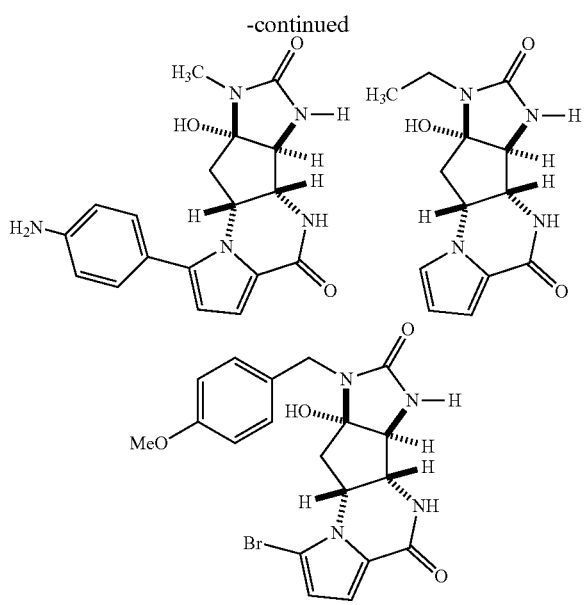

or a pharmaceutically acceptable salt thereof.

In some embodiments, the compound of formula (I) is selected from the group consisting of:

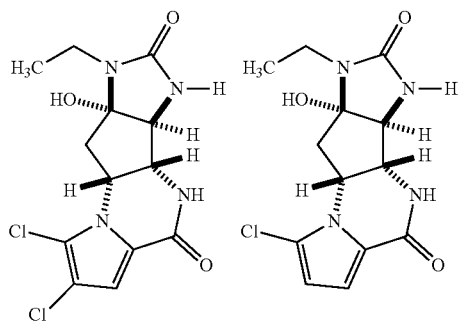

or a pharmaceutically acceptable salt thereof.

Also provided herein is a pharmaceutical composition comprising a compound of formula (I), or a pharmaceutically acceptable salt thereof, and a pharmaceutically acceptable carrier.

Further provided herein is a method for treating a primary or secondary brain tumor, said method comprising administering to a patient a therapeutically effective amount of a compound of formula (I):

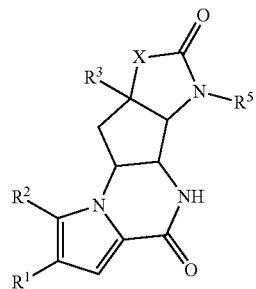

or a pharmaceutically acceptable salt thereof, wherein:

X is O or $NR^4$;

$R^1$ and $R^2$ are independently selected from the group consisting of: H, F, Cl, Br, I, substituted or unsubstituted $C_{1-6}$ alkyl, substituted or unsubstituted cycloalkyl, substituted or unsubstituted aryl, substituted or unsubstituted heterocycloalkyl, and substituted or unsubstituted heteroaryl;

$R^3$ is selected from the group consisting of: H, OH, and $O(C_{1-6}$ alkyl); and $R^4$ and $R^5$ are independently selected from the group consisting of: H and substituted or unsubstituted $C_{1-6}$ alkyl.

Non-limiting examples of a compound of formula (I) for the treatment of primary and secondary brain tumors include:

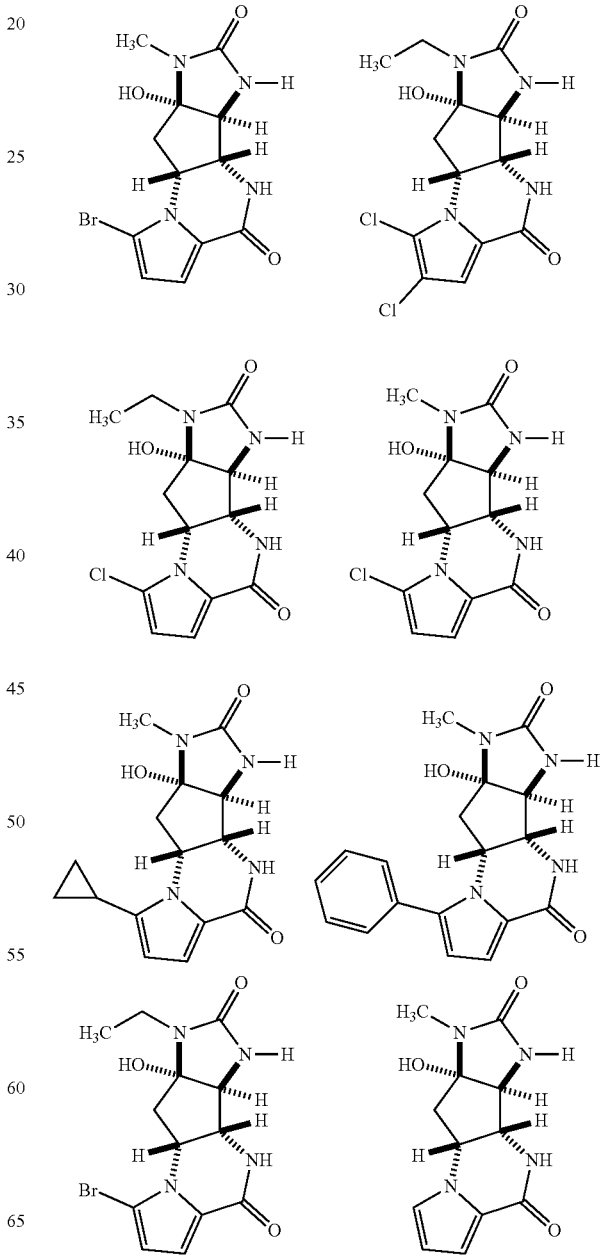

-continued

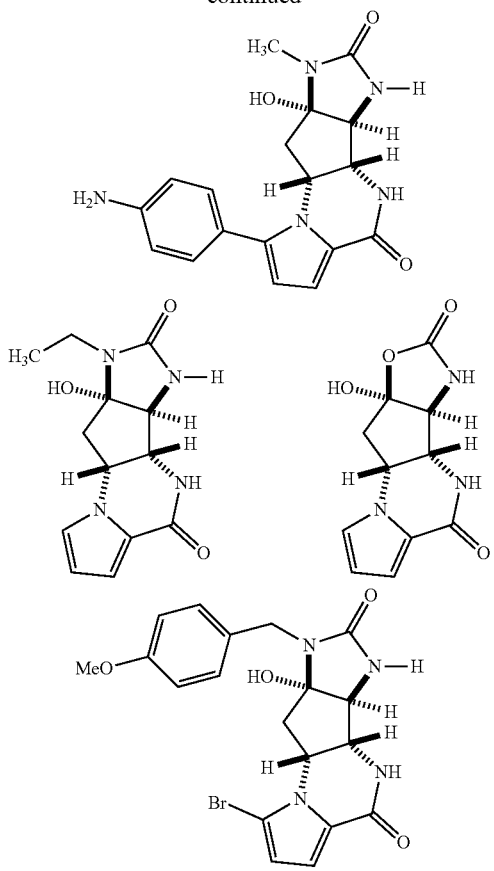

or a pharmaceutically acceptable salt thereof.

This disclosure also provides a compound of formula (II):

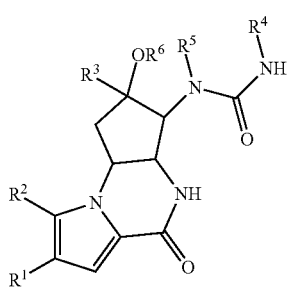

or a pharmaceutically acceptable salt thereof,
wherein:
$R^1$ and $R^2$ are independently selected from the group consisting of: H, F, Cl, Br, I, substituted or unsubstituted $C_{1-6}$ alkyl, substituted or unsubstituted cycloalkyl, substituted or unsubstituted aryl, substituted or unsubstituted heterocycloalkyl, and substituted or unsubstituted heteroaryl;
$R^3$ is selected from the group consisting of: H, OH, and $O(C_{1-6}$ alkyl);
$R^4$, $R^5$, and $R^6$ are independently selected from the group consisting of: H and substituted or unsubstituted $C_{1-6}$ alkyl; and
wherein at least one of $R^1$ and $R^2$ is not H.

In some embodiments, the compound of formula (II) is:

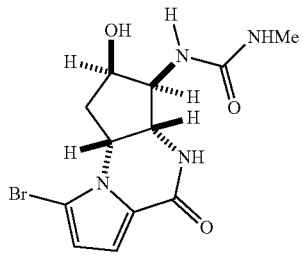

or a pharmaceutically acceptable salt thereof.

Pharmaceutical compositions comprising a compound of formula (II) can be prepared and include the compounds and a pharmaceutically acceptable carrier.

Further provided herein is a method for treating a primary or secondary brain tumor, said method comprising administering to a patient a therapeutically effective amount of a compound of formula (II):

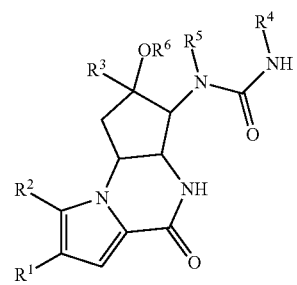

or a pharmaceutically acceptable salt thereof,
wherein:
$R^1$ and $R^2$ are independently selected from the group consisting of: H, F, Cl, Br, I, substituted or unsubstituted $C_{1-6}$ alkyl, substituted or unsubstituted cycloalkyl, substituted or unsubstituted aryl, substituted or unsubstituted heterocycloalkyl, and substituted or unsubstituted heteroaryl;
$R^3$ is selected from the group consisting of: H, OH, and $O(C_{1-6}$ alkyl);
$R^4$, $R^5$, and $R^6$ are independently selected from the group consisting of: H and substituted or unsubstituted $C_{1-6}$ alkyl.

Non-limiting examples of a compound of formula (II) for the treatment of a primary or secondary brain tumor include:

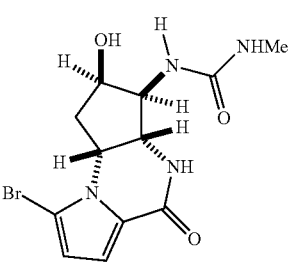

and

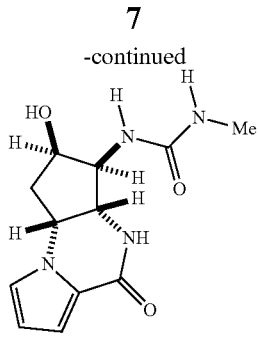

or a pharmaceutically acceptable salt thereof.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 illustrates that Agelastatin A (AA) has anti-lymphoma activity.

FIG. 2 shows the results of central nervous system pharmacokinetic analysis in mice illustrating that Agelastatin A (AA) can penetrate the central nervous system.

FIG. 3 illustrates the results from preclinical evaluation of Agelastatin A (AA) in murine orthotopic central nervous system (CNS) lymphoma model, created by intracerebral injection of 25,000 luciferase-transfected Raji lymphoma cells in athymic mice. AA has a therapeutic effect against CNS lymphoma with prolongation of survival. FIG. 3A provides evidence for a therapeutic effect of AA treatment on the CNS lymphoma growth as shown by Bioluminescence imaging (BLI). FIG. 3B shows quantitation of BLI on days 4, 8, 12, 15 and 22 post-intracerebral injection in the control group (vehicle, N=6), T1 group (Agelastatin A 1 mg/kg i.p. N=8), T2 group (Agelastatin A 2.5 mg/kg i.p. N=8) and T3 group (Agelastatin A 5 mg/kg i.p. N=8). *, P<0.05 as compared with control group. **, P<0.001 as compared with control group. FIG. 3C is the Kaplan-Meier analysis showing survival prolongation associated with AA treatment (p<0.05, n=5).

FIG. 4 shows that Agelastatin A (AA) decreases the dissemination of Raji lymphoma cells inside the brain. Assessment was made in the brain hemisphere contralateral to the tumor implantation site. CD20 immunohistochemistry (IHC) was used to identify the lymphoma cells. CD20-stained lymphoma cells were counted using Aperio ImageScope in lateral, anterior and posterior compartments of the contralateral brain hemisphere. FIG. 4A shows the assessment of the impact of AA treatment on lateral dissemination of lymphoma cells. Three compartments (C1-3) were selected from central to lateral in the contralateral brain for counting the lymphoma cells. AA treatments in T2 and T3 groups decreased lateral dissemination of lymphoma cells. FIG. 4B shows the assessment of the impact of AA treatment on lymphoma cell dissemination in the anterior and posterior direction in the contralateral brain. Dissemination of lymphoma cells was decreased in all the treatment groups. FIG. 4C shows CD20 IHC illustrating lateral, anterior and posterior dissemination of lymphoma cells in the contralateral brain for control, T1, T2 and T3.

FIG. 5 illustrates that Agelastatin A (AA) shows anti-osteopontin (OPN) activity via downregulation of OPN transcription and suppresses NFkB signaling in Raji lymphoma cells. FIG. 5A shows that AA decreases OPN secretion by Raji cells (* p<0.001; ** p<0.0001). ELISA was used to measure OPN secretion into the culture medium. FIG. 5B shows that AA decreases the expression of OPN messenger RNA (mRNA) at 12 h (* P<0.0001). mRNA was measured by PCR. FIG. 5C shows the results of NFkB reporter assay illustrating that AA treatment attenuates the NFkB signaling in Raji cells. FIG. 5D shows that AA treatment decreased the NFkB signaling activity of Raji cells, which had been transfected with NFkB reporter and implanted in the murine brain. Right panel: Bioluminescence imaging (BLI) of NFkB signaling activity of Raji lymphoma cells in the brain on day 4 post Raji cell implantation. Left panel: Quantitation of BLI on days 0, 1, 2, 3 and 4 post-intracerebral injection of 25,000 Raji lymphoma (n=5, *, P<0.05 as compared with control). Mice in two treatment groups received AA 2.5 mg/kg and 5 mg/kg intraperitoneally the day after the implantation.

FIG. 6 shows the results of a CNS pharmacokinetics analysis of AA (FIG. 6A), CAA (FIG. 6B), CEAA (FIG. 6C), and DCEAA (FIG. 6D). Samples were collected by in vivo microdialysis at various time points after intravenous injection of 2.5 mg kg-1 of AA or analogues. Drug levels were measured in serum and cerebrospinal fluid (CSF) by capillary electrophoresis. Shown are means and SEMs (N=6). CNS penetration is calculated as a ratio of area under the curve (AUC) of CSF and serum drug concentrations.

FIG. 7 illustrates significant therapeutic activity of Agelastatin A and its analogues (CAA, CEAA, and DCEAA)

against CNS lymphoma with prolongation of survival in cell line-derived (OCI-LY10) orthotopic murine xenograft model. FIG. 7A shows bioluminescence imaging of CNS lymphoma on day 21 post tumor implantation. FIG. 7B shows the luminescence signal of lymphoma growth post-intracerebral injection of 1×105 OCI-LY10 cells. The data were shown as mean±SEM (average radiance % baseline) for n=5. In vivo tumor growth in AA-2.5 mg/kg, AA-5 mg/kg, CAA-2.5 mg/kg, CEAA-2.5 mg/kg, CEAA-5 mg/kg, DCEAA-2.5 mg/kg and DCEAA-5 mg/kg groups were significantly slower than that in the control group. *, P<0.05, as compared with control. FIG. 7C provides the kaplan-Meier analysis that shows prolongation of survival with AA-2.5 mg/kg, AA-5 mg/kg, CAA-2.5 mg/kg, CEAA-2.5 mg/kg, CEAA-5 mg/kg, DCEAA-2.5 mg/kg and DCEAA-5 mg/kg treated groups (p<0.05, n=5).

FIG. 8 shows significant therapeutic activity of AA and its analogues (CAA, CEAA, and DCEAA) against triple-negative metastatic breast cancer of the brain with prolongation of survival in cell line-derived (MB-468) orthotopic murine xenograft model. FIG. 8A shows bioluminescence imaging of triple-negative metastatic breast cancer cells on day 21 post tumor implantation. FIG. 8B shows the luminescence signal of lymphoma growth post-intracerebral injection of 1×105 MB-468 cells. The data were shown as mean±SEM (average radiance % baseline) for n=5. In vivo tumor growth in AA-2.5 mg/kg, AA-5 mg/kg, CEAA-2.5 mg/kg, CEAA-5 mg/kg, DCEAA-2.5 mg/kg and DCEAA-5 mg/kg groups were significantly slower than that in the control group. *, P<0.05, as compared to control. FIG. 8C provides the Kaplan-Meier analysis and shows prolongation of survival with AA-2.5 mg/kg, AA-5 mg/kg, CEAA-2.5 mg/kg, CEAA-5 mg/kg, DCEAA-2.5 mg/kg and DCEAA-5 mg/kg treated groups (p<0.05, n=5).

FIG. 9 shows significant therapeutic activity of AA and its analogues (CAA, CEAA, and DCEAA) against Glioblastoma multiforme with prolongation of survival in cell line-derived (U87) orthotopic murine xenograft model. FIG. 9A shows bioluminescence imaging of Glioblastoma cells on day 18 post tumor implantation. FIG. 9B shows the luminescence signal of lymphoma growth post-intracerebral injection of 1.75×105 U87 cells. The data were shown as mean±SEM (average radiance % baseline) for n=5. In vivo tumor growth in AA-2.5 mg/kg, AA-5 mg/kg, CAA-2.5 mg/kg, CEAA-2.5 mg/kg, CEAA-5 mg/kg, DCEAA-2.5 mg/kg and DCEAA-5 mg/kg groups were significantly slower than that in the control group. *, P<0.05, as compared to control. FIG. 9C provides the Kaplan-Meier analysis and shows prolongation of survival with AA-2.5 mg/kg, AA-5 mg/kg, CAA-2.5 mg/kg, CEAA-2.5 mg/kg, CEAA-5 mg/kg, DCEAA-2.5 mg/kg and DCEAA-5 mg/kg treated groups (p<0.05, n=5).

DETAILED DESCRIPTION

Definitions

Figure 1A:
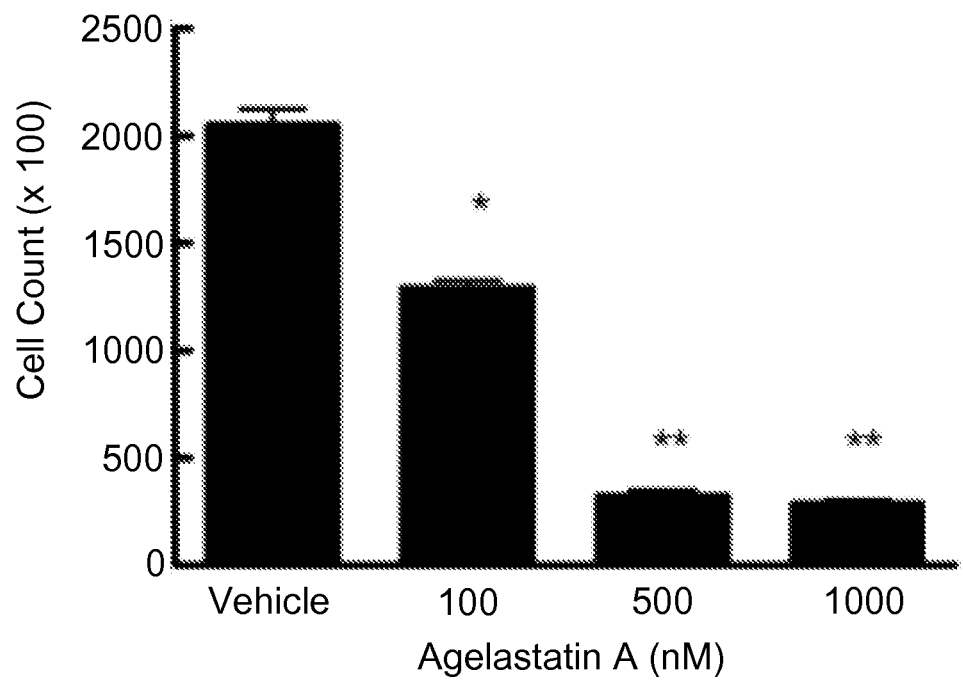
FIG. 1A. Cell proliferation assay illustrates that AA decreases Raji lymphoma cell proliferation.
Figure 1B:
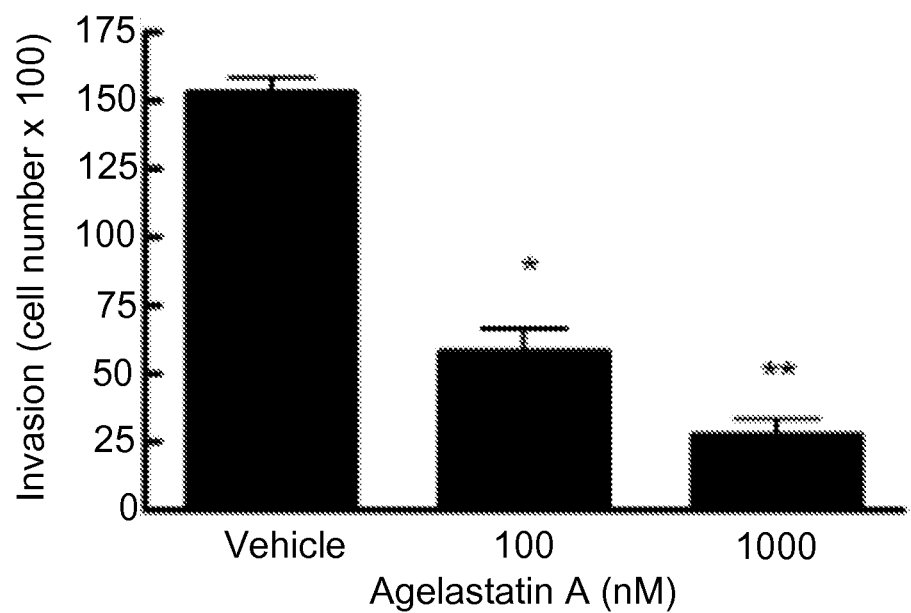
FIG. 1B. Matrigel invasion assay shows that AA blocks Raji lymphoma cell invasion.
Figure 1C:
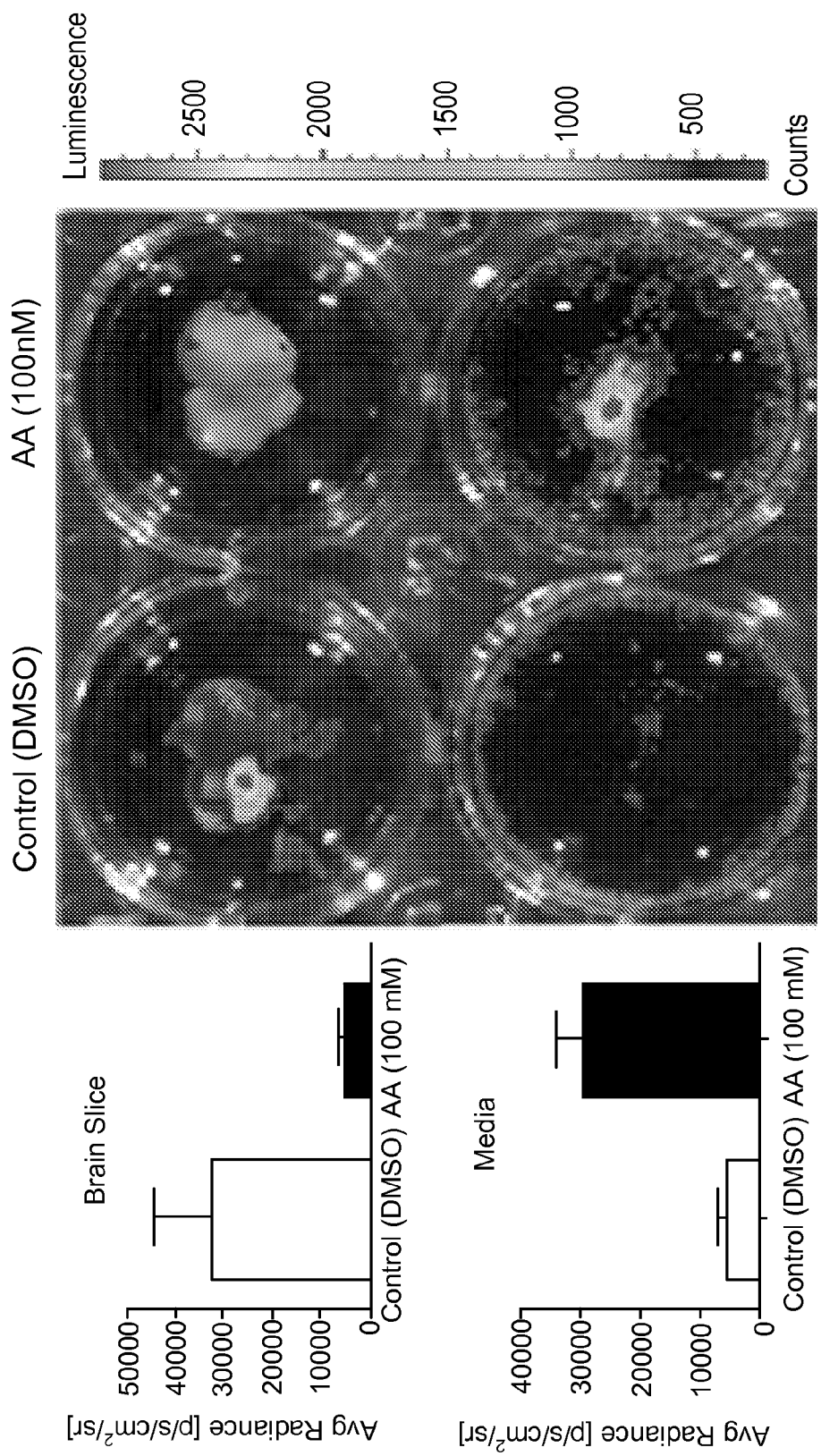
FIG. 1C. Ex vivo brain slice invasion assay shows that AA treatment decreases the brain invasiveness of Raji lymphoma cells. Bioluminescence imaging (BLI) (right panel) and quantitation of BLI (left panel) of the ex vivo brain slice and the media are shown. The assessment was performed on day 5 post-incubation of 25,000 Raji cells pretreated with DMSO or 100 nM of AA for four days.
Figure 1D:
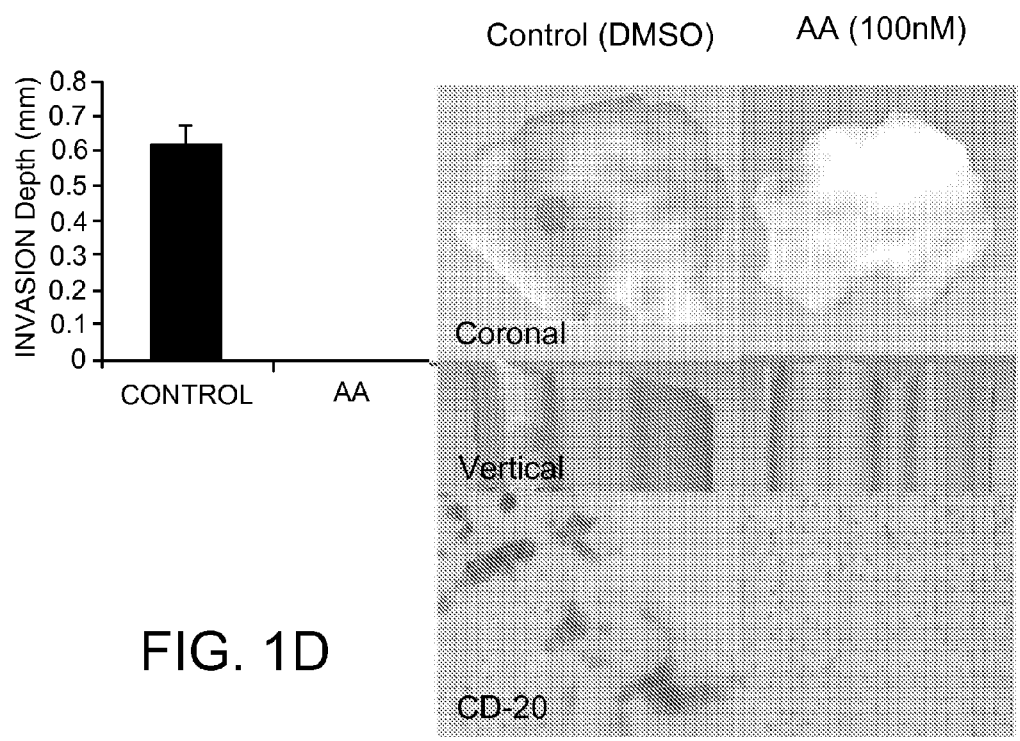
FIG. 1D. Luminescent tomography and IHC show that AA prevents Raji lymphoma cells from invading the brain slice. No AA-treated lymphoma cells were found in the brain slice. Luminescent tomography (coronal and lateral view) and CD-20 staining of the brain slice on day 5 post-incubation of 25,000 Raji cells pretreated with DMSO or 100 nM AA for four days (right panel) is shown. Source voxels are displayed on a red-black color scale in units of photons/sec. The left panel shows the quantitation of invasive depth in the brain slice. Shown are mean±SEM for n=3. *, p<0.05, as compared with DMSO group.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "patient," as used herein, includes both humans and other animals, particularly mammals. Thus, the methods are applicable to both human therapy and veterinary applications. In some embodiments, the patient is a mammal, for example, a primate. In some embodiments, the patient is a human.

The terms "treating" and "treatment" mean causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

A "therapeutically effective" amount of the inhibitors described herein is typically one which is sufficient to achieve the desired effect and may vary according to the nature and severity of the disease condition, and the potency of the inhibitor. It will be appreciated that different concentrations may be employed for prophylaxis than for treatment of an active disease.

The term "contacting" means bringing at least two moieties together, whether in an in vitro system or an in vivo system.

The term "inhibition" with respect to osteopontin (OPN) refers to inhibition of OPN and its biological activities associated with the OPN pathway. Inhibition of OPN can include antagonizing or inactivation. The mode of action of an OPN inhibitor can be direct, e.g., through binding to OPN as a ligand. Inhibition also can be indirect, e.g., through binding to and/or modifying another molecule that otherwise binds to and activates OPN.

As used herein, "administration" refers to delivery of a compound provided herein or composition comprising a compound provided herein by any external route, including, without limitation, IV, intramuscular, SC, intranasal, inhalation, transdermal, oral, buccal, rectal, sublingual, and parenteral administration.

A compound provided herein can also incorporate one or more isotopes of the atoms occurring in the compound. Isotopes include, for example, those atoms having the same atomic number but different mass numbers. For example, carbon atoms can include carbon-12, carbon-13, and/or carbon-14 and hydrogen atoms can include hydrogen, deuterium, and/or tritium.

The term, "compound," as used herein is meant to include all stereoisomers, geometric isomers, and tautomers of the structures depicted. Compounds herein identified by name or structure as one particular tautomeric form are intended to include other tautomeric forms unless otherwise specified.

In some embodiments, a compound provided herein, or a pharmaceutically acceptable salt thereof, is substantially isolated. By "substantially isolated" is meant that the compound is at least partially or substantially separated from the environment in which it was formed or detected. Partial separation can include, for example, a composition enriched in the compound provided herein. Substantial separation can include compositions containing at least about 50%, at least about 60%, at least about 70%, at least about 80%, at least about 90%, at least about 95%, at least about 97%, or at least about 99% by weight of the a compound provided herein, or a pharmaceutically acceptable salt thereof. Methods for isolating compounds and their pharmaceutically acceptable salts are routine in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "alkyl" includes straight-chain alkyl groups (e.g., methyl, ethyl, propyl, butyl, pentyl, hexyl, heptyl, octyl, nonyl, decyl, etc.) and branched-chain alkyl groups (isopropyl, tert-butyl, isobutyl, etc.). In certain embodiments, a straight chain or branched chain alkyl has six or fewer carbon atoms in its backbone (e.g., $C_{1-6}$ for straight chain; $C_{3-6}$ for branched chain). The term $C_{1-6}$ includes alkyl groups containing 1 to 6 carbon atoms.

The term "cycloalkyl" includes a cyclic aliphatic group which may be saturated or unsaturated. For example, cycloalkyl groups include cyclopropyl, cyclopentyl, cyclohexyl, cycloheptyl, and cyclooctyl. In some embodiments, cycloalkyls can have from 3-8 carbon atoms in their ring structure, for example, they can have 3, 4, 5, or 6 carbons in the ring structure.

In general, the term "aryl" includes groups, including 5- and 6-membered single-ring aromatic groups, such as benzene and phenyl. Furthermore, the term "aryl" includes multicyclic aryl groups, e.g., tricyclic and bicyclic groups, such as naphthalene and anthracene.

The term "heteroaryl" includes groups, including 5- and 6-membered single-ring aromatic groups, that have from one to four heteroatoms, for example, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "heteroaryl" includes multicyclic heteroaryl groups, e.g., tricyclic, bicyclic, such as benzoxazole, benzodioxazole, benzothiazole, benzoimidazole, benzothiophene, methylenedioxyphenyl, quinoline, isoquinoline, napthyridine, indole, benzofuran, purine, benzofuran, quinazoline, deazapurine, indazole, or indolizine.

The term "heterocycloalkyl" includes groups, including but not limited to, 3- to 10-membered single or multiple non-aromatic rings having one to five heteroatoms, for example, piperazine, pyrrolidine, piperidine, or homopiperazine.

The term "substituted" means that an atom or group of atoms replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. In some cases, two sites of substitution may come together to form a 3-10 membered cycloalkyl or heterocycloalkyl ring.

Substituents include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, substituted phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —$NR^9C(O)$—($C_1$-$C_{10}$ alkyl), —C(O)—($C_1$-$C_{10}$ alkyl), $C_2$-$C_{10}$ alkthioalkyl, —C(O)O—($C_1$-$C_{10}$ alkyl), —OH, —$SO_2$, =S, —COOH, —$NR^9_2$, carbonyl, —C(O)—($C_1$-$C_{10}$ alkyl)-$CF_3$, —C(O)—$CF_3$, —$C(O)NR^9_2$, —($C_1$-$C_{10}$ aryl)-S—($C_6$-$C_{10}$ aryl), —C(O)—($C_6$-$C_{10}$ aryl), —$(CH_2)_m$—O—$(CH_2)_m$—O—($C_1$-$C_{10}$ alkyl) wherein each m is from 1 to 8, —$C(O)NR^9_2$, —$C(S)NR^9_2$, —$SO_2NR^9_2$, —$NR^9C(O)NR^9_2$, —$NR^9C(S)NR^9_2$, salts thereof, and the like. Each $R^9$ group in the preceding list independently includes, but is not limited to, H, alkyl or substituted alkyl, aryl or substituted aryl, or alkylaryl. Where substituent groups are specified by their conventional chemical formulas, written from left to right, they equally encompass the chemically identical substituents that would result from writing the structure from right to left, for example, —$CH_2O$— is equivalent to —$OCH_2$—.

Also provided herein are pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; in some embodiments, a non-aqueous media like ether, ethyl acetate, alcohols (e.g., methanol, ethanol, iso-propanol, or butanol) or acetonitrile (ACN) can be used. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. Conventional methods for preparing salt forms are described, for example, in *Handbook of Pharmaceutical Salts: Properties, Selection, and Use,* Wiley-VCH, 2002.

Compounds

Provided herein are compounds of formula (I):

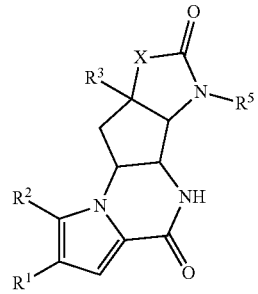

or a pharmaceutically acceptable salt thereof, wherein:

X is O or $NR^4$;

$R^1$ and $R^2$ are independently selected from the group consisting of: H, F, Cl, Br, I, substituted or unsubstituted $C_{1-6}$ alkyl, substituted or unsubstituted cycloalkyl, substituted or unsubstituted aryl, substituted or unsubstituted heterocycloalkyl, and substituted or unsubstituted heteroaryl;

$R^3$ is selected from the group consisting of: H, OH, and O($C_{1-6}$ alkyl); and $R^4$ and $R^5$ are independently selected from the group consisting of: H and substituted or unsubstituted $C_{1-6}$ alkyl.

In some embodiments, if $R^1$ is H, $R^2$ is Br, $R^3$ is OH, and $R^5$ is H, then $R^4$ is not $CH_3$. In some embodiments, if $R^1$ is H, $R^2$ is H, $R^3$ is OH, and $R^5$ is H, then $R^4$ is not $CH_3$. In some embodiments, if $R^1$ is H, $R^2$ is H, $R^3$ is H, and $R^5$ is H, then X is not O. For example, in some cases, a compound of formula (I) does not include:

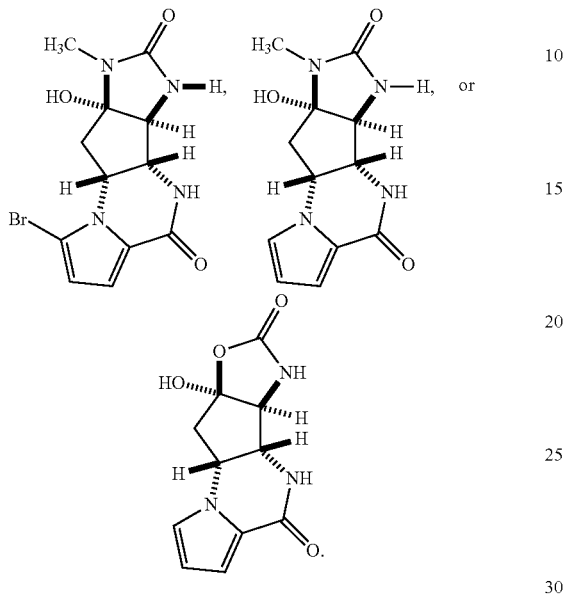

In some embodiments, X is $NR^4$. In certain of these embodiments, $R^4$ is a $C_{1-6}$ alkyl such as methyl or ethyl. For example, X can be selected from the group consisting of: $N(CH_3)$ and $N(CH_2CH_3)$.

In some embodiments, $R^1$ and $R^2$ are independently selected from H and Cl.

In some embodiments, $R^3$ is OH.

Non-limiting examples of a compound of formula (I) include:

AA

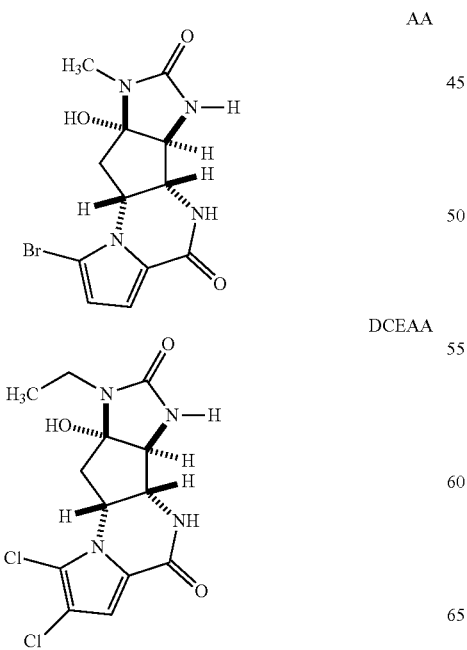

DCEAA

CEAA

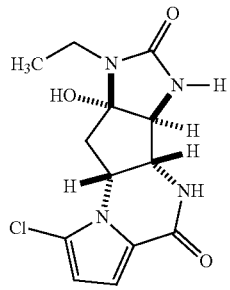

CAA

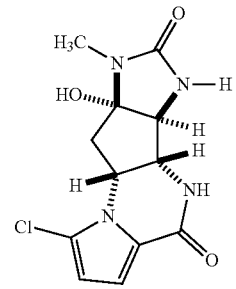

CPAA

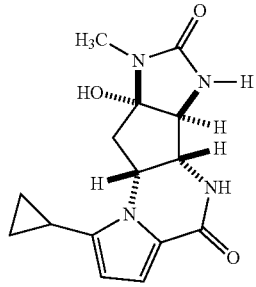

PAA

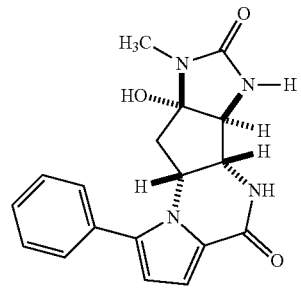

EAA

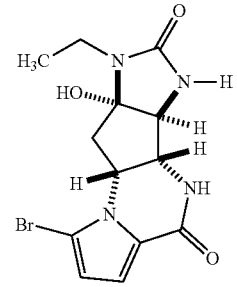

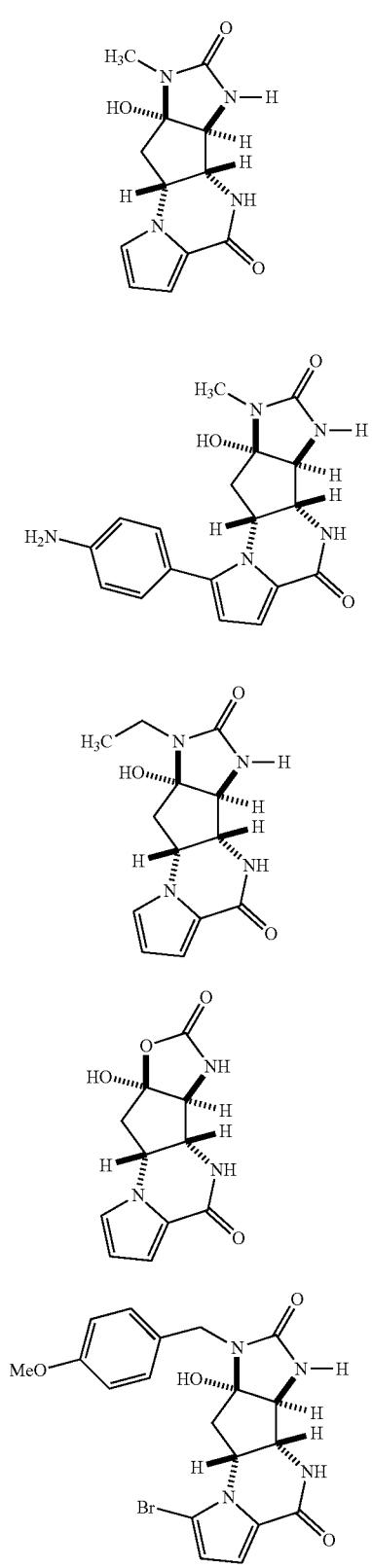

or a pharmaceutically acceptable salt thereof.

In some embodiments, a compound of formula (I) is selected from the group consisting of:

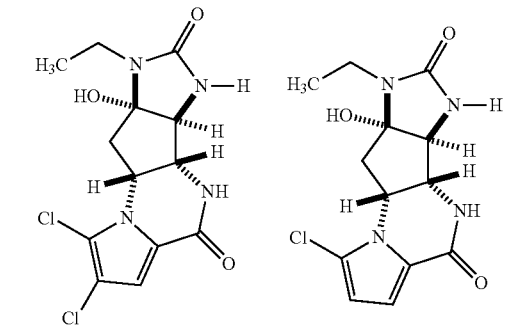

or a pharmaceutically acceptable salt thereof.

Also provided herein is a compound of formula (II):

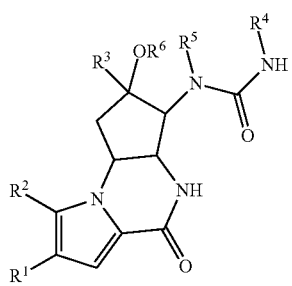

or a pharmaceutically acceptable salt thereof,
wherein:

R¹ and R² are independently selected from the group consisting of: H, F, Cl, Br, I, substituted or unsubstituted $C_{1-6}$ alkyl, substituted or unsubstituted cycloalkyl, substituted or unsubstituted aryl, substituted or unsubstituted heterocycloalkyl, and substituted or unsubstituted heteroaryl;

R³ is selected from the group consisting of: H, OH, and $O(C_{1-6}$ alkyl);

R⁴, R⁵, and R⁶ are independently selected from the group consisting of: H and substituted or unsubstituted $C_{1-6}$ alkyl.

In some embodiments, at least one of R¹ and R² is not H. For example, in some embodiments, a compound of formula (II) is not:

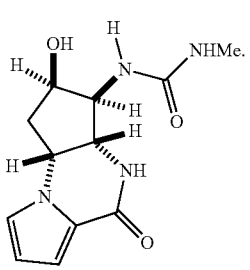

In some embodiments, R¹ and R² are selected from the group consisting of H and Br. In some embodiments, R³ is H. In some embodiments, R⁴, R⁵, and R⁶ are independently selected from H and CH₃.

A non-limiting example of a compound of formula (II) includes:

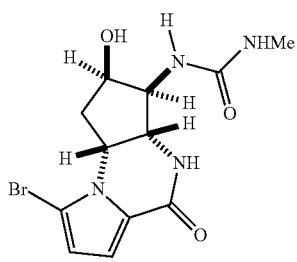

or a pharmaceutically acceptable salt thereof.

Synthetic Methods

The compounds provided herein, including pharmaceutically acceptable salts thereof, can be prepared using known organic synthesis techniques and can be synthesized according to any of numerous possible synthetic routes. In general, a compound of formula (I) or (II) is conveniently obtained via standard organic chemistry synthesis methods. For example, a compound of formula (I) may be prepared as shown in Schemes 1-4 or as described in Example 5.

Scheme 2. Synthesis of AA analogues (CAA).

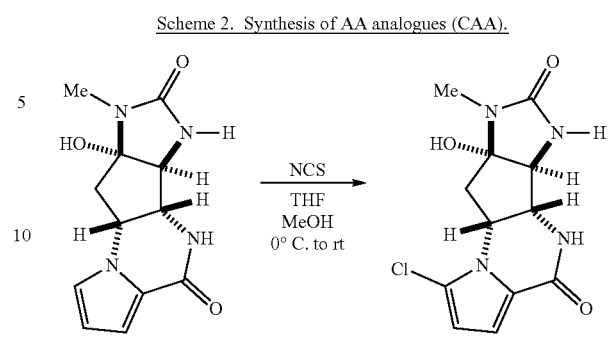

Scheme 1. Synthesis of AA analogues.

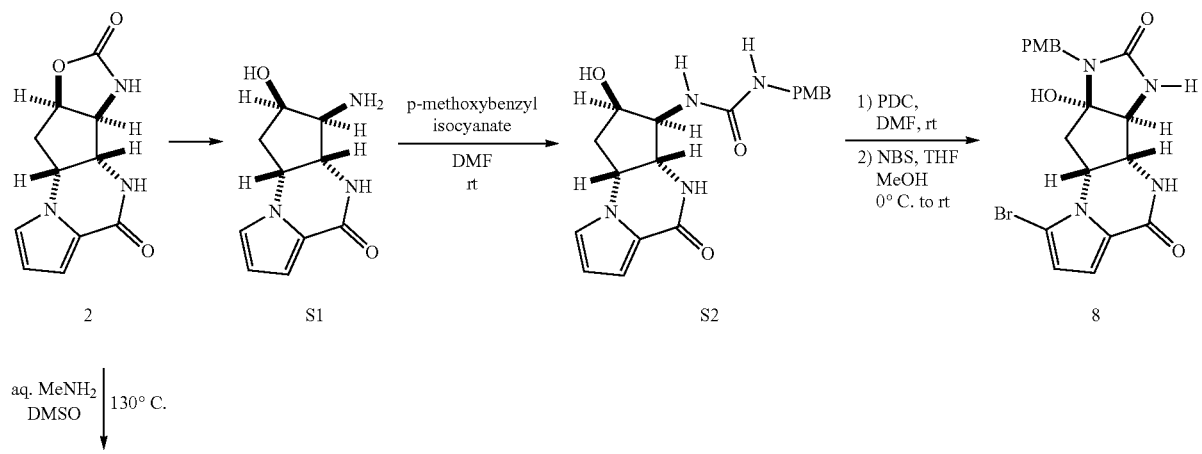

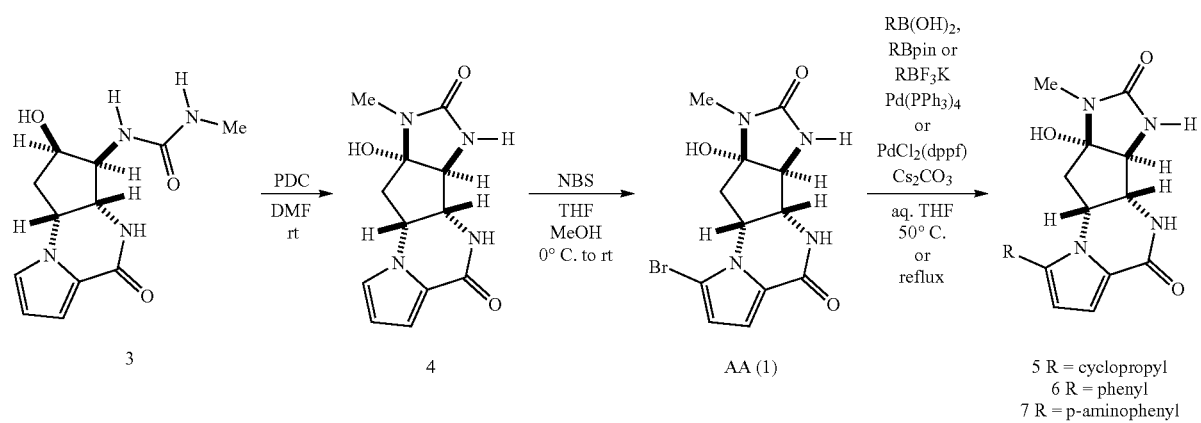

5 R = cyclopropyl
6 R = phenyl
7 R = p-aminophenyl

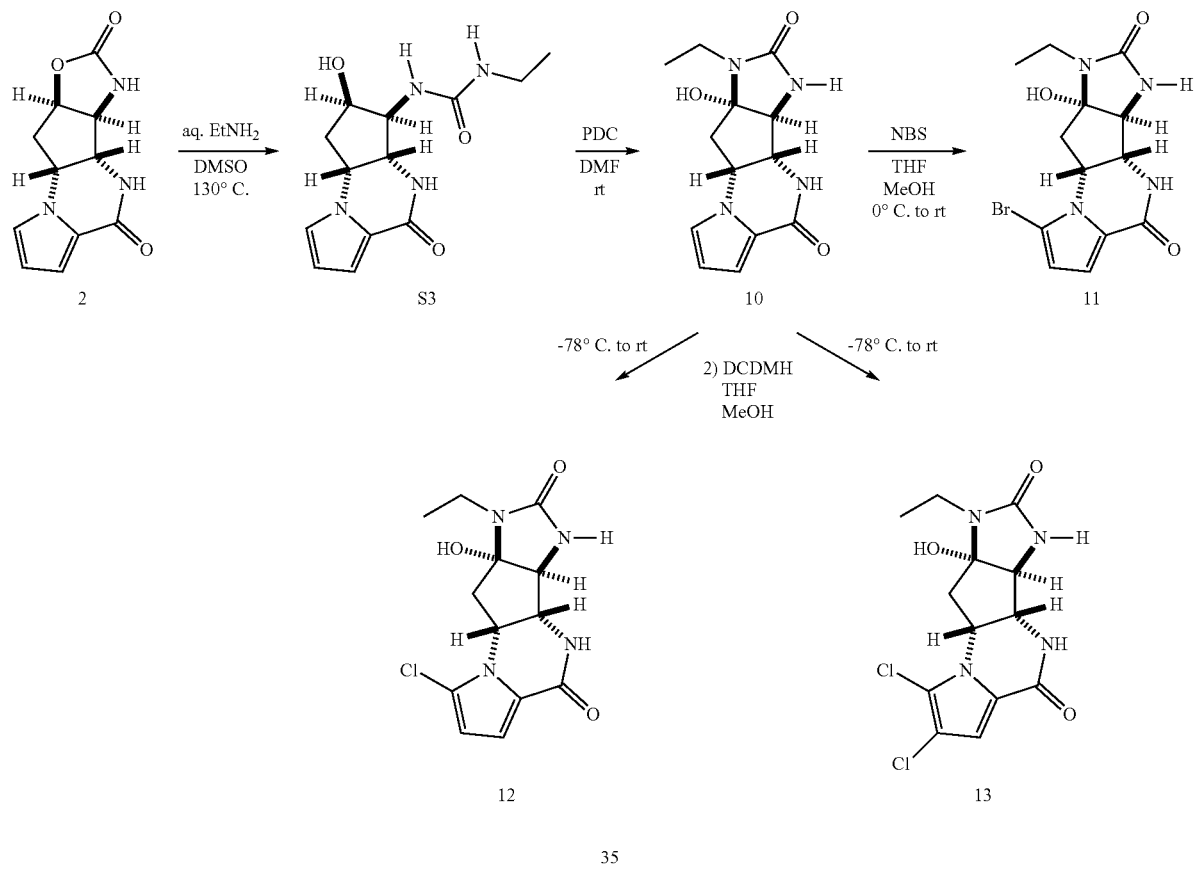

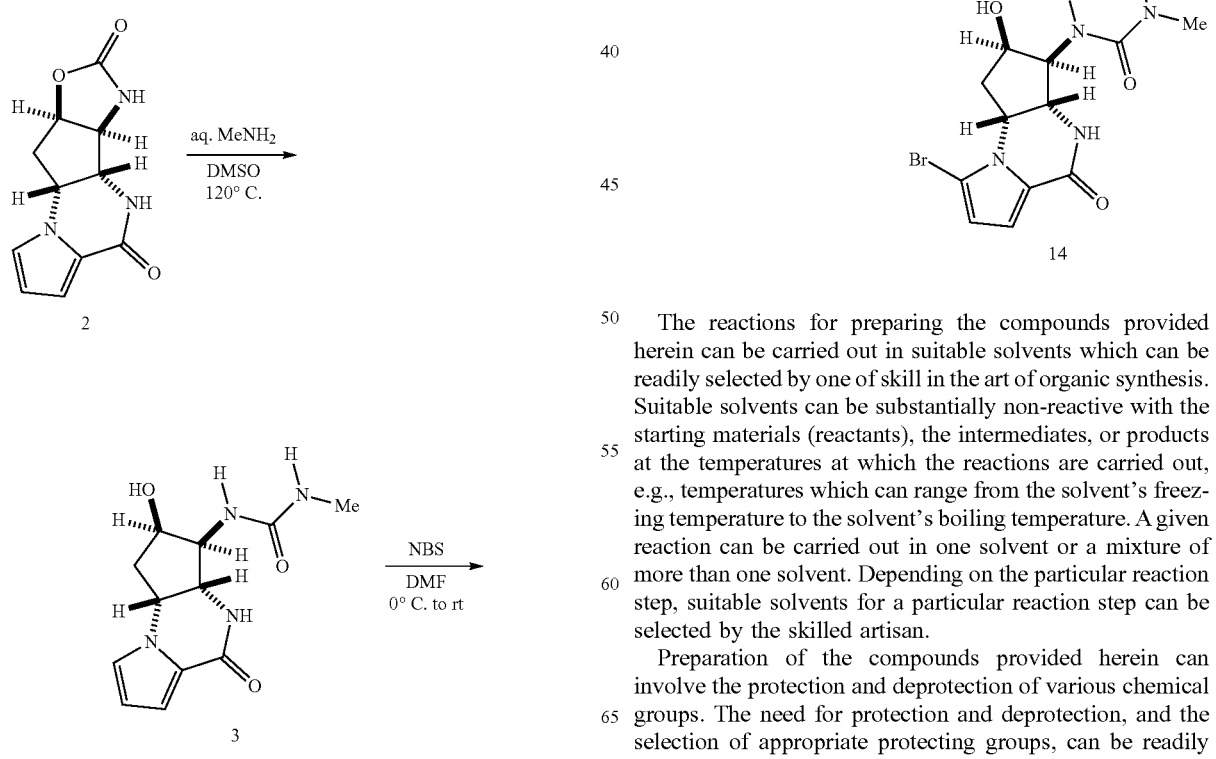

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry*, 1$^{st}$ Ed., Oxford University Press, 2000; *March's Advanced Organic Chemistry: Reactions, Mechanisms, and Structure*, 5$^{th}$ Ed., Wiley-Interscience Publication, 2001; and Peturssion, S. et al., "*Protecting Groups in Carbohydrate Chemistry*," *J. Chem. Educ.*, 74(11), 1297 (1997) (each of which is incorporated herein by reference in its entirety).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874 (2004), which is incorporated herein by reference in its entirety) and normal phase silica chromatography.

Pharmaceutical Formulations and Dosage Forms

When employed as pharmaceuticals, the compounds provided herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal, intramuscular or injection or infusion; or intracranial, e.g., intrathecal or intraventricular, administration. Parenteral administration can be in the form of a single bolus dose, or may be, for example, by a continuous perfusion pump. In some embodiments, administration is systemic administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also provides pharmaceutical compositions which contain, as the active ingredient, a compound provided herein or a pharmaceutically acceptable salt thereof, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, an active compound can be milled to provide the appropriate particle size prior to combining with the other ingredients. If an active compound is substantially insoluble, it can be milled to a particle size of less than 200 mesh. If an active compound is substantially water soluble, the particle size can be adjusted by milling to provide a substantially uniform distribution in the formulation, e.g. about 40 mesh.

The compounds provided herein may be milled using known milling procedures such as wet milling to obtain a particle size appropriate for tablet formation and for other formulation types. Finely divided (nanoparticulate) preparations of the compounds provided herein can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions provided herein can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid preformulation composition containing a homogeneous mixture of a compound provided herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient provided herein.

The tablets or pills provided herein can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions provided herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

In some embodiments, the compounds provided herein are formulated for intravenous administration. Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin. In some embodiments, the pharmaceutical composition is administered systemically.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound provided herein. The topical formulations can be suitably packaged in tubes of, for example, 100 g which are optionally associated with instructions for the treatment of the select indication.

In one embodiment, the compounds provided herein are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions provided herein contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions provided herein contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions provided herein contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses provided herein.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The therapeutic dosage of a compound provided herein can vary according to, for example, the particular use for which the treatment is made, the manner of administration of the compound, the health and condition of the patient, and the judgment of the prescribing physician. The proportion or concentration of a compound provided herein in a pharmaceutical composition can vary depending upon a number of factors including dosage, chemical characteristics (e.g., hydrophobicity), and the route of administration. For example, the compounds provided herein can be provided in an aqueous physiological buffer solution containing about 0.1 to about 10% w/v of the compound for parenteral administration. Some typical dose ranges are from about 1 mg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Methods of Use

Provided herein are methods of treating a brain or nervous systems cancer (e.g., a brain tumor) in a patient. In some embodiments, the method comprises administering a therapeutically effective amount of a compound as provided herein to the patient.

In some embodiments, a compound provided herein can be used to treat a brain cancer. In some embodiments, the brain cancer is a primary or secondary brain tumor. Non-limiting examples of brain cancers include: primary CNS lymphoma (PCNSL), glioblastoma multiforme (GBM), astrocytoma, medulloblastoma, glioma, ependymoma, germinoma (pinealoma), oligodendroglioma, schwannoma, retinoblastoma, congenital tumors, and a metastatic brain tumor of systemic cancers such as metastatic breast cancer of the brain. In some embodiments, the brain cancer is PCNSL or GBM.

In some embodiments, a compound provided herein can be used to treat a cancer of the spinal cord. For example, a neurofibroma, meningioma, or glioma.

In some embodiments, the patient is a human.

In some embodiments, the patient has a cancer associated with resistance to a known anticancer drug regime, e.g., glioblastoma multiforme (GBM).

A method of treating cancer using a compound of formula (I) or (II) may be combined with existing methods of treating cancers, for example by chemotherapy, irradiation, or surgery. In some embodiments, a compound of formula (I) or (II) can be administered before, during, or after another anticancer agent or treatment.

In some embodiments (e.g., when compositions comprising a compound of formula (I) or (II) are administered in conjunction with another anticancer agent), one can create a synergistic effect among the agents administered and thereby improve the outcome for a patient. In some embodiments, a compound of formula (I) or (II) (or a pharmaceutically acceptable salt form thereof) can be administered in combination with (i.e., before, during, or after) administration of a pain relief agent (e.g., a nonsteroidal anti-inflammatory drug such as celecoxib or rofecoxib), an antinausea agent, or an additional anticancer agent (e.g., paclitaxel, docetaxel, doxorubicin, daunorubicin, epirubicin, fluorouracil, melphalan, cis-platin, carboplatin, cyclophosphamide, mitomycin, methotrexate, mitoxantrone, vinblastine, vincristine, ifosfamide, teniposide, etoposide, bleomycin, leucovorin, taxol, herceptin, avastin, cytarabine, dactinomycin, interferon alpha, streptozocin, prednisolone, irinotecan, sulindac, 5-fluorouracil, capecitabine or procarbazine). In certain embodiments, the anticancer agent is selected from the group consisting of: AFINITOR (Everolimus), AFINITOR DISPERZ (Everolimus), AVASTIN (Bevacizumab), Bevacizumab, CEENU (Lomustine), Everolimus, Lomustine, METHAZOLASTONE (Temozolomide), TEMODAR (Temozolomide), and Temozolomide.

Without being bound by theory, a compound provided herein may treat a brain or nervous system cancer as described herein by crossing the blood-brain barrier. In some embodiments, the compounds provided herein are able to inhibit OPN in a patient.

The compounds provided herein are effective to inhibit OPN in a cell, for example, in a cancer cell (e.g., in a cell from a brain tumor). Therefore there is also provided a method of inhibiting OPN in a cell comprising contacting the cell with an effective amount of a compound provided herein, or a pharmaceutically acceptable salt form thereof. The method may be performed by contacting the cell with a compound as described herein, or a pharmaceutically acceptable salt form thereof, in vitro, thereby inhibiting OPN in vitro. Uses of such an in vitro method of inhibiting OPN include, but are not limited to use in a screening assay (for example, wherein a compound described herein is used as a positive control or standard compared to compounds of unknown activity or potency in inhibiting OPN).

In some embodiments, the compounds provided herein dowregulate the expression of messenger RNA (mRNA) of osteopontin. In some embodiments, the compounds provided herein downregulate the NFKB pathway.

Also provided herein are methods of treating other forms of cancer, for example, prostate cancer, breast cancer, and lymphoma using compounds provided herein. In some embodiments, the method comprises administering a therapeutically effective amount of a compound as provided herein to the patient.

Prostate cancer as used herein can include, for example, adenocarcinoma, small cell carcinoma, and rarer prostate cancer types.

Breast cancer as used herein can include, for example, ER+ breast cancer, ER− breast cancer, her2− breast cancer, her2+ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative (ER−), progesterone receptor negative, and her2 positive (her2+). In some embodiments, the breast cancer may have a high risk Oncotype score. In some embodiments, the breast cancer is selected from ER+ breast cancer, ER− breast cancer, her2+ breast cancer, her2− breast cancer, and triple negative breast cancer.

Lymphoma as used herein can include, for example, precursor T-cell lymphoma, follicular lymphoma, diffuse large B cell lymphoma, mantle cell lymphoma, B-cell chronic lymphocytic lymphoma, MALT lymphoma, Burkitt's lymphoma, Mycosis fungoides, peripheral T-cell lymphoma, and Hodgkin's lymphoma.

EXAMPLES

Example 1

Preparation of Compounds

General.

Melting points are uncorrected. All reagents were used as received from commercial suppliers unless otherwise noted. $^1$H NMR spectra (500 or 400 MHz) and $^{13}$C NMR spectra (125 or 100 MHz) were measured in CD$_3$OD unless otherwise stated. Chemical shifts are reported in ppm relative to the internal solvent signal: Methanol-d: 3.30 ppm ($^1$H NMR), 49.0 ppm ($^{13}$C NMR)]. The proton signal of TMS (0.00 ppm) or DMSO (2.50 ppm) was also used in some cases as the internal standard for $^1$H NMR spectra. FT-IR spectra were recorded for samples loaded on KBr powder using the diffuse reflectance method. Mass spectra were obtained according to the specified technique. Analytical thin layer chromatography (TLC) was performed using Kieselgel 60 F$_{254}$. Compounds were visualized with UV light and stained with anisaldehyde solution, phosphomolybdic acid in EtOH, iodine, or KMnO$_4$ solution. The preparation of compounds 1, 2, 3, 4 and S1 has previously been reported. All the spectroscopic and analytical data for the known compounds described in the present paper are completely identical with those previously reported.

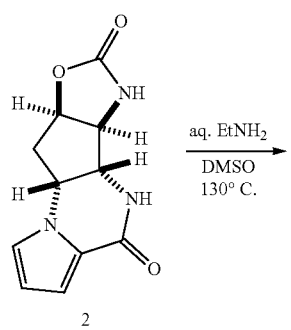

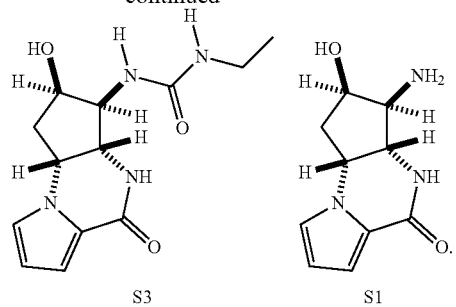

To a solution of compound 2 (36.4 mg, 0.165 mmol) in DMSO (2.28 mL) in a stainless steel tube was added 70% aq. EtNH$_2$ (2.28 mL, 28 mmol) at room temperature, and the mixture was heated at 130° C. for 10 h. Additional 70% aq. EtNH$_2$ (0.5 mL, 6.14 mmol) was added and heating was continued at 130° C. for further 6 h. After concentration of the mixture under reduced pressure, the residue was rinsed with MeOH to leave unreacted compound 2 (11.8 mg, 32% recovered) as a colorless solid. Concentration of the MeOH extracts under reduced pressure followed by flash column chromatography (MeOH/CH$_2$Cl$_2$ 1:6→1:5 v/v) of the resultant residue afforded hydroxyurea S3 (18.7 mg, 43%) as a colorless solid. Further elution using MeOH as eluent afforded aminoalcohol S1 (5.7 mg, 18%) as a colorless solid. Hydroxyurea S3: colorless solid; $[\alpha]^{25}_D$ −177.0 (c 0.565, MeOH); IR (KBr) ν 3279, 1634 cm$^{-1}$; $^1$H NMR (400 MHz, CD$_3$OD) δ 7.00 (dd, 1H, J=2.7, 1.8 Hz), 6.85 (dd, 1H, J=3.7, 1.8 Hz), 6.27 (dd, 1H, J=3.7, 2.7 Hz), 4.70 (dt, 1H, J=6.9, 4.6 Hz), 4.17 (m, 1H), 3.97 (m, 2H), 3.13 (q, 2H, J=7.3 Hz), 2.52 (m, 1H), 2.38 (ddd, 1H, J=15.1, 7.3, 2.7 Hz), 1.09 (t, 3H, J=7.3 Hz); $^{13}$C NMR (125 MHz, CD$_3$OD) δ 161.35, 160.83, 124.45, 123.55, 114.83, 111.51, 69.35, 60.59, 59.43, 53.12, 41.00, 35.80, 15.66; MS m/z: 279 (M+H), 93 (100%); HRMS (FAB) calcd for C$_{13}$H$_{19}$N$_4$O$_3$(M+H$^+$): 279.1457. found: 279.1483. The spectral and analytical data of aminoalcohol S1 have been previously reported.

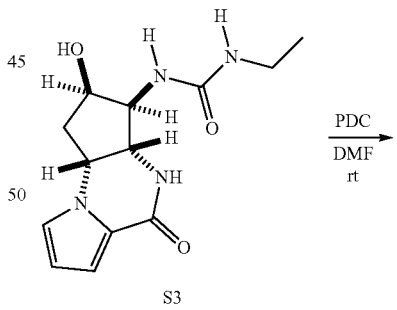

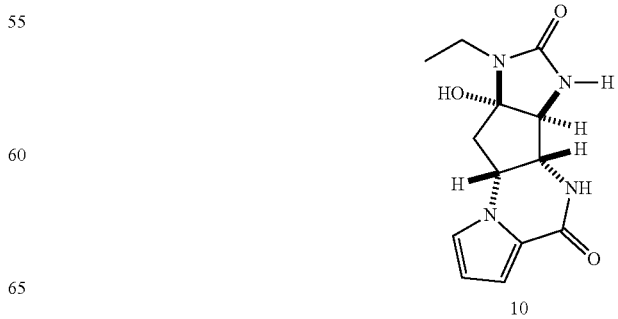

To a stirred solution of hydroxyurea S3 (32.3 mg, 0.116 mmol) in DMF (3.3 mL) was added pyridinium dichromate (PDC) (131 mg, 0.35 mmol). After stirring at room temperature for 73 h, i-PrOH (27 μL) was added, and the mixture was stirred for additional 10 min and concentrated under reduced pressure. The residue was charged onto a column of flash silica gel/florisil (slurry packed) and eluted with MeOH/CH$_2$Cl$_2$ (1:12 v/v) to give debromoethylagelastatin A (DeBEAA) (10) (18 mg, 57%) as a colorless solid. Compound 10: Colorless solid; $[\alpha]^{25}_D$ −54.4 (c 0.20, MeOH); IR (KBr) v 3236, 1653 cm$^{-1}$; $^1$H NMR (400 MHz, CD$_3$OD) δ 7.02 (dd, 1H, J=2.8, 1.2 Hz), 6.88 (dd, 1H, J=3.6, 1.2 Hz), 6.23 (dd, 1H, J=3.6, 2.8 Hz), 4.65 (ddd, 1H, J=10.0, 6.0, 6.0 Hz), 3.99 (dd, 1H, J=4.8, 1.2 Hz), 3.77 (d, 1H, J=1.2 Hz), 3.36 (m, 1H), 3.20 (m, 1H), 2.59 (dd, 1H, J=13.2, 6.4 Hz), 2.37 (dd, 1H, J=13.2, 10.0 Hz), 1.25 (t, 3H, J=7.2 Hz); $^{13}$C NMR (125 MHz, CD$_3$OD) δ 162.00, 161.28, 125.61, 122.94, 115.44, 111.13, 96.37, 68.31 62.96, 55.66, 42.86, 35.20, 15.87; MS m/z: 277 (M+H$^+$), 154 (100%); HRMS (FAB) calcd for C$_{13}$H$_{17}$N$_4$O$_3$(M+H$^+$): 277.1301. found: 277.1310.

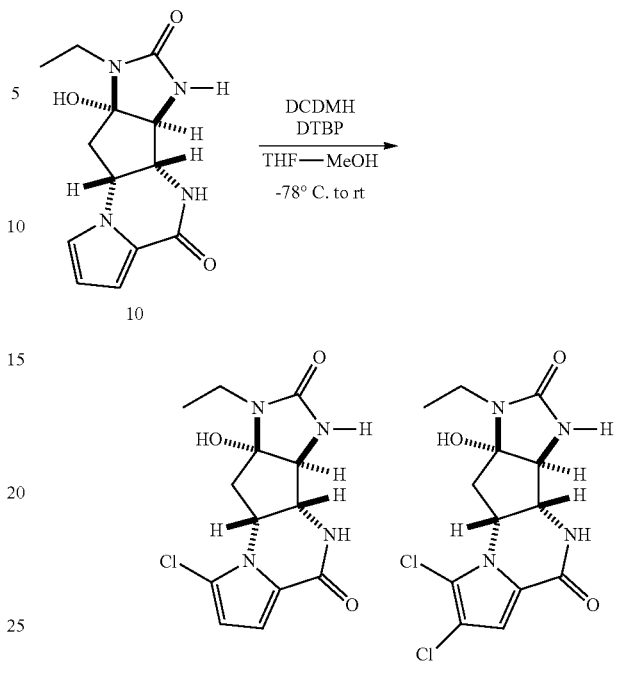

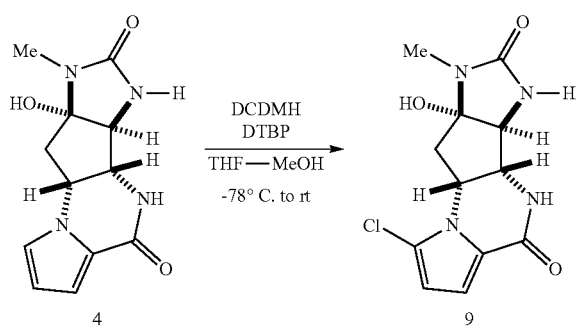

To a stirred solution of debromoagelastatin A (DeBAA) (4) (170 mg, 0.648 mmol) in THF-MeOH (122.4 mL; 2:1 v/v) in a dry ice/acetone cooling bath (−78° C.) were added 2,6-di-tert-butylpyridine (DTBP) (218 μL; 0.972 mmol) and dichlorodimethylhydantoin (DCDMH) (115 mg in THF-MeOH 3 mL; 2:1 v/v, 0.153 mmol). Following removal of the dry ice/acetone bath, stirring was continued for 100 min at room temperature. The mixture was quenched with Et$_3$N (903 μL; 6.48 mmol) and 2-methyl-2-butene (686 μL; 6.48 mmol), and concentrated under reduced pressure. The residue was purified by flash silica gel column chromatography (MeOH/EtOAc/H$_2$O 1:30:1 v/v/v) to give chloroagelastatin A (CAA) (9) (135 mg, 70%) as a colorless solid. Compound 9: colorless solid; $[\alpha]^{25}_D$ −29.1 (c 0.225, MeOH); IR (KBr) v 3333, 1636 cm$^{-1}$; $^1$H NMR (400 MHz, CD$_3$OD) δ 6.85 (d, 1H, J=4.1 Hz), 6.19 (d, 1H, J=4.1 Hz), 4.58 (ddd, 1H, J=12.4, 6.4, 5.5 Hz), 4.04 (d, 1H, J=5.5 Hz), 3.83 (s, 1H), 2.75 (s, 3H), 2.59 (dd, 1H, J=13.3, 6.4 Hz), 2.06 (dd, 1H, J=12.8, 12.4 Hz); $^{13}$C NMR (100 MHz, CD$_3$OD) δ 161.42, 161.13, 122.43, 120.70, 115.33, 109.96, 95.76 67.43, 62.26, 53.10, 40.01, 24.22; MS m/z: 297 (M+H), 93 (100%); HRMS (FAB) calcd for C$_{12}$H$_{14}$ClN$_4$O$_3$ (M+H$^+$): 297.0754. found: 297.0762.

To a stirred solution of debromoethylagelastatin A (DeBEAA) (10) (247 mg, 0.894 mmol) in THF-MeOH (177 mL; 2:1 v/v) in a dry ice/acetone cooling bath (−78° C.) were added 2,6-di-tert-butylpyridine (DTBP) (0.3 mL; 1.34 mmol) and dichlorodimethylhydantoin (DCDMH) (176 mg in THF-MeOH 4.5 mL; 2:1 v/v, 0.894 mmol). Following removal of the dry ice/acetone bath, stirring was continued for 60 min at room temperature. The mixture was quenched with Et$_3$N (1.2 mL; 8.94 mmol) and 2-methyl-2-butene (0.9 mL; 8.94 mmol), and concentrated under reduced pressure. The residue was purified by flash silica gel column chromatography (MeOH/EtOAc/H$_2$O 1:30:1 v/v/v) to give chloroethylagelastatin A (CEAA) (12) (184 mg, 66%) as a colorless solid and dichloroethylagelastatin A (DCEAA) (13) (27 mg, 9%) as a colorless solid. Chloroethylagelastatin A (CEAA) 12: colorless solid; $[\alpha]^{25}_D$ −59.6 (c 0.355, MeOH); IR (KBr) v 3265, 1664 cm$^{-1}$; $^1$H NMR (400 MHz, CD$_3$OD) δ 6.89 (d, 1H, J=4.3 Hz), 6.23 (d, 1H, J=4.3 Hz), 4.65 (ddd, 1H, J=12.2, 6.1, 4.9 Hz), 4.07 (d, 1H, J=4.9 Hz), 3.84 (s, 1H), 3.37-3.23 (m, 2H), 2.62 (dd, 1H, J=12.8, 6.1 Hz), 2.18 (dd, 1H, J=12.8, 12.2 Hz), 1.27 (t, 3H, J=7.3 Hz); $^{13}$C NMR (125 MHz, CD$_3$OD) δ 161.44, 161.07, 122.46, 120.59, 115.30, 109.97, 96.11, 67.52, 62.38, 53.03, 41.00, 34.88, 15.91; MS m/z: 311 (M+H$^+$), 93 (100%); HRMS (FAB) calcd for C$_{13}$H$_{16}$ClN$_4$O$_3$(M+H$^+$): 311.0911. found: 311.0905. Dichloroethylagelastatin A (DCEAA) (13): colorless solid; $[\alpha]^{25}_D$ −47.2 (c 0.445, MeOH); IR (KBr) v 3352, 1653 cm$^{-1}$; $^1$H NMR (400 MHz, CD$_3$OD) δ 6.87 (s, 1H), 4.64 (ddd, 1H, J=12.4, 6.0, 5.6 Hz), 4.10 (d, 1H, J=5.6 Hz), 3.83 (s, 1H), 3.36-3.23 (m, 2H), 2.64 (dd, 1H, J=12.8, 6.0 Hz), 2.19 (dd, 1H, J=12.8, 12.4 Hz), 1.27 (t, 3H, J=6.8 Hz); $^{13}$C NMR (100 MHz, CD$_3$OD) δ161.38, 159.96, 121.75, 117.71, 113.78, 112.77, 96.03, 67.54, 62.20, 53.63, 40.93, 34.90, 15.93; MS m/z: 345 (M+H$^+$), 93 (100%); HRMS (FAB) calcd for C$_{13}$H$_{15}$Cl$_2$N$_4$O$_3$(M+H$^+$): 345.0521. found: 345.0527.

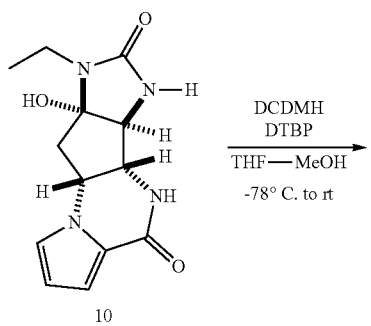

10

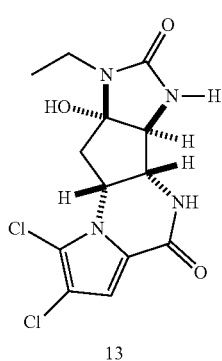

13

To a stirred solution of debromoethylagelastatin A (De-BEAA) (10) (205 mg, 0.742 mmol) in THF-MeOH (147 mL; 2:1 v/v) in a dry ice/acetone cooling bath (−78° C.) were added 2,6-di-tert-butylpyridine (DTBP) (0.5 mL; 2.23 mmol) and dichlorodimethylhydantoin (DCDMH) (292 mg in THF-MeOH 4 mL; 2:1 v/v, 1.48 mmol). Following removal of the dry ice/acetone bath, stirring was continued for 55 min at room temperature. The mixture was quenched with Et$_3$N (1.0 mL; 7.42 mmol) and 2-methyl-2-butene (0.8 mL; 7.42 mmol), and concentrated under reduced pressure. The residue was purified by flash silica gel column chromatography (MeOH/EtOAc/H$_2$O 1:30:1 v/v/v) to give dichloroethylagelastatin A (DCEAA) (13) (108 mg, 42%) as a colorless solid.

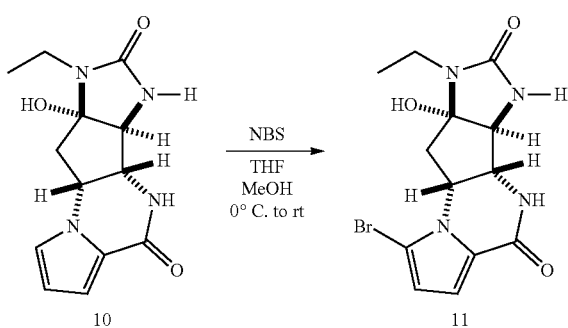

To a solution of debromoethylagelastatin A (DeBEAA) (10) (2.5 mg, 0.009 mmol) in THF-MeOH (1.5 mL; 2:1 v/v) was added NBS (1 mg in THF-MeOH 100 μL; 2:1 v/v, 0.005 mmol) at 0° C., and the mixture was allowed to warm to room temperature. After being stirred for 50 min, the mixture was again cooled to 0° C., and NBS (0.32 mg in THF-MeOH 100 μL; 2:1 v/v, 0.0018 mmol) was added. After stirring for additional 1 h at room temperature, the mixture was concentrated under reduced pressure. The residue was purified by flash silica gel column chromatography (MeOH/CH$_2$Cl$_2$ 1:10) to give ethylagelastatin A (EAA) (11) (2.1 mg, 65%) as a colorless solid. Compound 11: colorless solid; $[\alpha]^{25}_D$ −38.2 (c 0.055, MeOH); IR (KBr) ν 3381, 3069, 1655 cm$^{-1}$; $^1$H NMR (400 MHz, CD$_3$OD) δ 6.90 (d, 1H, J=4.1 Hz), 6.33 (dd, 1H, J=4.1 Hz), 4.63 (ddd, 1H, J=11.9, 6.0, 6.0 Hz), 4.08 (d, 1H, J=5.5 Hz), 3.84 (s, 1H), 3.37-3.24 (m, 1H), 2.63 (dd, 1H, J=12.8, 6.4 Hz), 2.16 (dd, 1H, J=12.8, 10.0 Hz), 1.30 (t, 3H, J=6.9 Hz); $^{13}$C NMR (100 MHz, CD$_3$OD) δ 161.5, 161.0, 124.2, 116.0, 113.8, 107.2, 96.0, 67.5, 62.3, 54.3, 41.1, 34.9, 16.0; MS m/z: 277 (M+H$^+$), 93 (100%); HRMS (FAB) calcd for C$_{13}$H$_{15}$BrN$_4$O$_3$ (M+H$^+$): 355.0406. found: 355.0423.

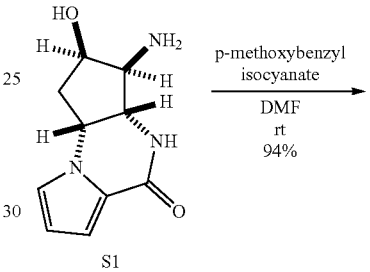

S1

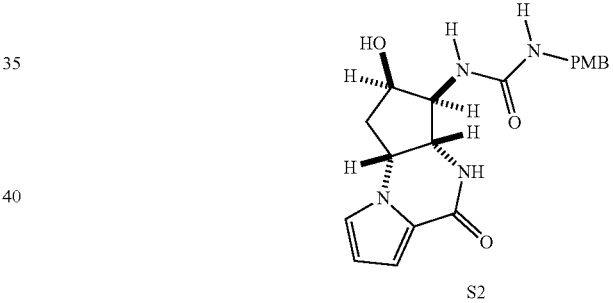

S2

To a solution of aminoalcohol S1 (9 mg, 0.0403 mmol) in DMF (1 mL) was added p-methoxybenzyl isocyanate (6.3 μL, 0.0443 mmol). After stirring for 80 min at room temperature, the mixture was concentrated under reduced pressure to give a sufficiently pure hydroxyurea S2 (14.1 mg, 94%) as a colorless solid. Compound S2: colorless solid; IR (KBr) ν 3285, 1636 cm$^{-1}$; $^1$H NMR (500 MHz, DMSO-d6) δ 7.72 (d, 1H, J=3.4 Hz), 7.16 (d, 2H, J=8.6 Hz), 7.04 (dd, 1H, J=2.3, 1.7 Hz), 6.86 (d, 2H, J=8.6 Hz), 6.69 (dd, 1H, J=6.3, 5.7 Hz), 6.61 (dd, 1H, J=4.0, 1.7 Hz), 6.18 (dd, 1H, J=3.4, 2.2 Hz), 5.93 (d, 1H, J=8.0 Hz), 5.32 (d, 1H, J=4.6 Hz), 4.57 (m, 1H), 4.16-4.09 (m, 2H), 3.97 (m, 1H), 3.83-3.73 (m, 2H), 3.71 (s, 3H), 2.42 (ddd, 1H, J=14.9, 6.3, 4.0 Hz), 2.22 (ddd, 1H, J=14.3, 7.4, 2.3 Hz); $^{13}$C NMR (125 MHz, DMSO-d6) δ 158.04, 157.69, 132.49, 128.47, 123.39, 122.44, 113.63, 111.84, 109.50, 67.37, 58.60, 57.42, 55.05, 51.39, 42.41; MS m/z: 371 (M+H$^+$), 93 (100%); HRMS (FAB) calcd for C$_{19}$H$_{23}$N$_4$O$_4$(M+H$^+$): 371.1719. found: 371.1728.

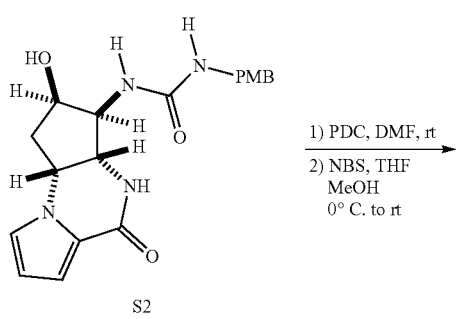

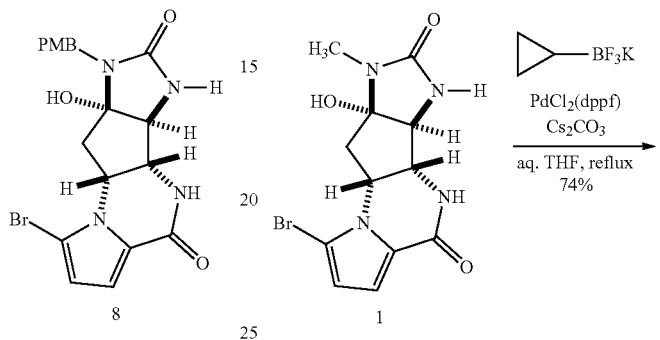

To a stirred solution of hydroxyurea S2 (10 mg, 0.027 mmol) in DMF (1 mL) at room temperature was added pyridinium dichromate (PDC) (30.5 mg, 0.081 mmol), and the mixture was stirred at room temperature. After 28 h, i-PrOH (6.2 µL) was added, and the mixture was stirred for additional 10 min and concentrated under reduced pressure. The residue was charged onto a column of flash silica gel/florisil (slurry packed) and eluted with MeOH/CH$_2$Cl$_2$ (1:15 v/v) to give hemiaminal (structure not indicated) (3 mg, 30%) as a pale yellow solid. Hemiaminal: pale yellow solid; $[\alpha]^{25}_D$ −7.0 (c 0.165, MeOH); IR (KBr) ν 3457, 1633 cm$^{-1}$; $^1$H NMR (400 MHz, CD$_3$OD) δ 7.34 (d, 2H, J=8.7 Hz), 6.93 (d, 2H, J=8.7 Hz), 6.81 (dd, 1H, J=3.8, 1.4 Hz), 6.50 (dd, 1H J=2.3, 1.8 Hz), 6.15 (dd, 1H, J=3.8, 2.3 Hz), 4.64 (d, 1H, J=15.6 Hz), 4.40 (m, 1H), 4.20 (d, 1H, J=15.6 Hz), 3.96 (dd, 1H, J=5.0, 1.4 Hz), 3.81-3.76 (m, 4H), 2.18-2.10 (m, 2H); $^{13}$C NMR (100 MHz, CD$_3$OD) δ161.87, 161.57, 160.67, 132.67, 130.29, 124.94, 122.84, 115.29, 115.01, 111.11, 95.83, 68.08, 62.83, 55.77, 55.38, 42.43, 42.26; MS m/z: 369 (M+H$^+$), 93 (100%); HRMS (FAB) calcd for C$_{19}$H$_{21}$N$_4$O$_4$(M+H$^+$): 369.1563. found: 369.1549.

To a solution of hemiaminal (structure not indicated) (1.6 mg, 0.004 mmol) in THF-MeOH (0.75 mL; 2:1 v/v) was added NBS (0.386 mg in THF-MeOH 100 µL; 2:1 v/v, 0.0022 mmol) at 0° C., and the mixture was allowed to warm to room temperature. After being stirred for 15 min, the mixture was again cooled to 0° C., and NBS (0.386 mg in THF-MeOH 100 µL; 2:1 v/v, 0.0022 mmol) was added. After stirring for additional 45 min at room temperature, the mixture was concentrated under reduced pressure. The residue was purified by flash silica gel column chromatography (MeOH/EtOAC/H$_2$O 1:80:1 v/v/v) to give N-p-methoxybenzyl agelastatin A (N-PMBAA) (8) (1.7 mg, 88%) as a colorless solid. Compound 8: colorless solid; $[\alpha]^{25}_D$ −5.8 (c 0.05, MeOH); IR (KBr) 3340, 1651 cm$^{-1}$; $^1$H NMR (400 MHz, CD$_3$OD) δ 7.36 (d, 2H, J=8.0 Hz), 6.90 (d, 2H, J=8.0 Hz), 6.82 (dd, 1H, J=4.0, Hz), 6.18 (d, 1H J=4.0 Hz), 4.66 (d, 1H, J=15.6 Hz), 4.40 (ddd, 1H, J=11.6, 6.0, 5.6 Hz), 4.15 (d, 1H, J=15.6 Hz), 4.05 (d, 1H, J=5.6 Hz), 3.87 (s, 1H), 3.77 (s, 3H), 2.35 (dd, 1H, J=12.8, 5.6 Hz), 1.93 (dd, 1H, J=12.8, 12.4 Hz); $^{13}$C NMR (100 MHz, CD$_3$OD) δ161.84, 160.98, 160.61, 133.00, 130.40, 124.01, 115.88, 115.44, 113.52, 107.08, 95.91, 67.77, 62.08, 55.78, 54.12, 42.14, 40.87; MS in/z: 447 (M+H$^+$), 93 (100%); HRMS (FAB) calcd for C$_{19}$H$_{20}$BrN$_4$O$_4$(M+H$^+$): 447.0668. found: 447.0667.

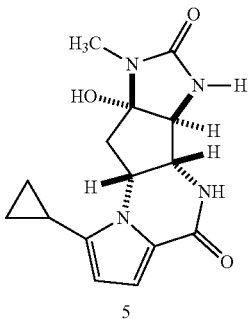

To a stirred solution of agelastatin A (1) (14.8 mg, 0.0434 mmol) in THF-H$_2$O (4 mL; 3:1 v/v) were added potassium cyclopropyl trifluoroborate (7.4 mg, 0.0521 mmol), Cs$_2$CO$_3$ (46.7 mg, 0.143 mmol), and PdCl$_2$(dppf) (17.7 mg, 0.0217 mmol). After stirring at 100° C. for 24 h, the mixture was cooled to room temperature and additional amounts of potassium cyclopropyl trifluoroborate (7.4 mg, 0.0521 mmol) and PdCl$_2$(dppf) (17.7 mg, 0.0217 mmol) were added. After stirring for additional 12 h at 100° C., the whole mixture was cooled to room temperature and transferred to a separatory funnel where it was partitioned between CH$_2$Cl$_2$ and H$_2$O. The aqueous layer was separated and concentrated. The residue was purified by flash silica gel column chromatography (MeOH/CH$_2$Cl$_2$ 1:7) to give cyclopropylagelastatin A (CPAA) (5) (9.7 mg, 74%) as a colorless solid. Compound 5: colorless solid; $[\alpha]^{25}_D$ −43.3 (c 0.065, MeOH); IR (KBr) ν 3383, 1633 cm$^{-1}$; $^1$H NMR (400 MHz, CD$_3$OD) δ 6.79 (d, 1H, J=4.0 Hz), 5.86 (d, 1H, J=4.0 Hz), 4.74 (ddd, 1H, J=11.6, 6.4, 6.0 Hz), 4.04 (d, 1H, J=5.2 Hz), 3.86 (s, 1H), 2.80 (s, 3H), 2.69 (dd, 1H, J=13.2, 6.4 Hz), 2.12 (dd, 1H, J=12.8, 12.4 Hz), 1.81 (m, 1H), 0.96-0.92 (m, 2H), 0.70 (m, 1H), 0.60 (m, 1H); $^{13}$C NMR (100 MHz, CD$_3$OD) δ 162.10, 161.51, 141.04, 121.88, 115.23, 107.50, 95.90, 67.53, 62.48, 52.99, 40.34, 24.20, 7.39, 7.19, 6.31; MS m/z: 303 (M+H$^+$), 93 (100%); HRMS (FAB) calcd for C$_{15}$H$_{19}$N$_4$O$_3$ (M+H$^+$): 303.1457. found: 303.1482.

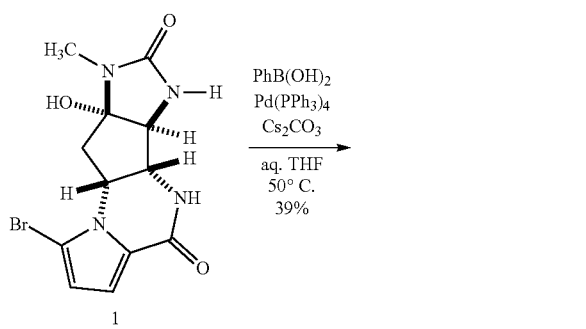

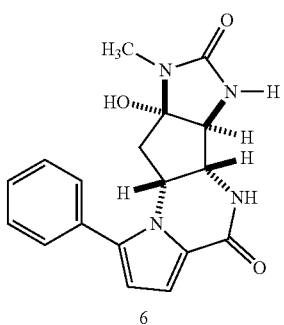

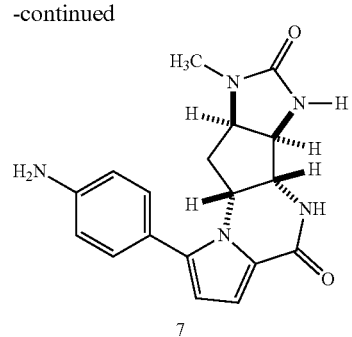

To a stirred solution of agelastatin A (1) (19.2 mg, 0.0563 mmol) in THF-H$_2$O (2 mL; 1:1 v/v) were added phenylboronic acid (20.6 mg, 0.169 mmol), Cs$_2$CO$_3$ (91.7 mg, 0.282 mmol), and Pd(PPh$_3$)$_4$ (19.5 mg, 0.0169 mmol). After stirring at 50° C. for 40 min, the mixture was cooled to room temperature and transferred to a reparatory funnel where it was partitioned between CH$_2$Cl$_2$ and H$_2$O. The aqueous layer was separated and concentrated. The residue was purified by flash silica gel column chromatography (MeOH/CH$_2$Cl$_2$ 1:8) to give phenylagelastatin A (PAA) (6) (7.4 mg, 39%) as a colorless solid. Compound 6: [α]$^{24}_D$ −82.8 (c 0.225, MeOH); IR (KBr) ν 3198, 1680 cm$^{-1}$; $^1$H NMR (400 MHz, CD$_3$OD) δ 7.51-7.38 (m, 5H), 6.99 (d, 1H, J=4.1 Hz), 6.32 (d, 1H, J=4.1 Hz), 4.52 (ddd, 1H, J=11.5, 6.0, 5.5 Hz), 4.05 (d, 1H, J=5.0 Hz), 3.83 (s, 1H), 2.58 (s, 3H), 2.38 (dd, 1H, J=13.2, 6.4 Hz), 2.19 (dd, 1H, J=12.8, 12.4 Hz); $^{13}$C NMR (125 MHz, CD$_3$OD) δ 162.13, 161.38, 139.28, 132.76, 129.96, 129.86, 129.68, 123.56, 115.98, 111.76, 95.41, 67.21, 62.43, 53.85, 40.82, 23.97; MS m/z: 339 (M+H$^+$), 93 (100%); HRMS (FAB) calcd for C$_{18}$H$_{19}$N$_4$O$_3$ (M+H$^+$): 339.1457. found: 339.1447.

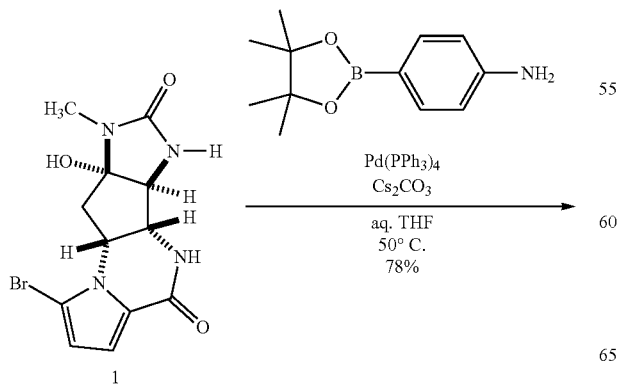

To a stirred solution of agelastatin A (1) (8.7 mg, 0.0255 mmol) in THF-H$_2$O (2 mL; 1:1 v/v) were added p-aminophenylboronic acid (6.1 mg, 0.0281 mmol), Cs$_2$CO$_3$ (41.5 mg, 0.128 mmol), and Pd(PPh$_3$)$_4$ (8.8 mg, 0.0077 mmol). After stifling at 50° C. for 1 h, the mixture was cooled to room temperature and concentrated under reduced pressure. The residue was purified by flash silica gel column chromatography (MeOH/CH$_2$Cl$_2$ 1:20) to give p-aminophenylagelastatin A (APAA) (7) (7 mg, 78%) as a pale yellow solid. Compound 7: [α]$^{25}_D$ −45.6 (c 0.05, MeOH); IR (KBr) ν 3288, 1647 cm$^{-1}$; $^1$H NMR (500 MHz, CD$_3$OD) δ 7.15 (d, 2H, J=8.5 Hz), 6.94 (d, 1H, J=4.5 Hz), 6.76 (d, 2H, J=8.5 Hz), 6.18 (d, 1H, J=4.5 Hz), 4.50 (ddd, 1H, J=11.5, 6.0, 5.5 Hz), 4.01 (d, 1H, J=4.5 Hz), 3.82 (s, 1H), 2.62 (s, 3H), 2.39 (dd, 1H, J=12.5, 6.0 Hz), 2.17 (dd, 1H, J=13.0, 12.5 Hz); $^{13}$C NMR (125 MHz, CD$_3$OD) δ 162.31, 161.42, 149.89, 140.34, 130.74, 122.50, 121.34, 116.08, 116.05, 110.91, 95.45, 67.16, 62.45, 53.67, 40.79, 24.04; MS m/z: 354 (M+H$^+$), 93 (100%); HRMS (FAB) calcd for C$_{18}$H$_{20}$N$_5$O$_3$ (M+H$^+$): 354.1566. found: 354.1570.

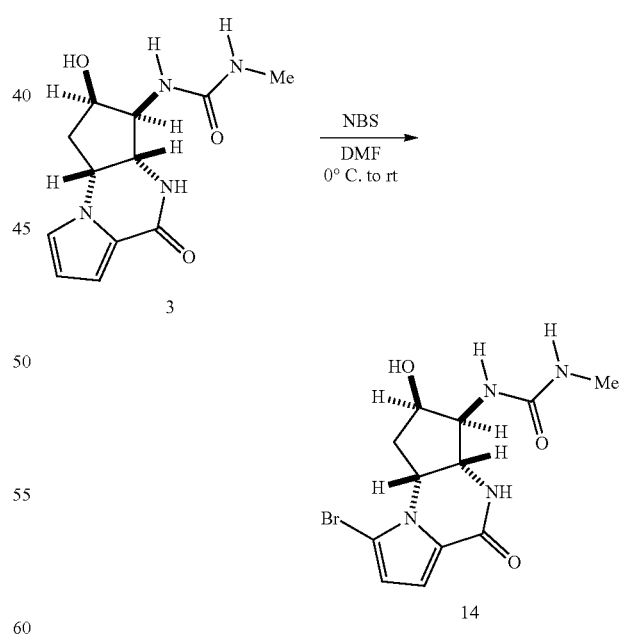

To a solution of hydroxyurea 3 (20 mg, 0.0757 mmol) in DMF (1 mL) at 0° C. was added NBS (13.5 mg, 0.0757 mmol). After stirring for 40 min at room temperature, the mixture was concentrated under reduced pressure. The residue was rinsed with EtOAc to leave sufficiently pure ureaagelastaitin A (UAA) (14) (25.4 mg, 97%) as a colorless solid. Compound 14: $[\alpha]^{25}_D$ −26.31 (c 0.245, MeOH); colorless solid; IR (KBr) v 3310, 1618 cm$^{-1}$; $^1$H NMR (500 MHz, CD$_3$OD) δ 6.82 (d, 1H, J=4.3 Hz), 6.27 (d, 1H, J=4.3 Hz), 4.93 (dt, 1H, J=10.4, 7.3 Hz), 4.34 (ddd, 1H, J=5.5, 4.9, 1.8 Hz), 4.08-4.02 (m, 2H), 2.67 (s, 3H), 2.44 (ddd, 1H, J=13.4, 7.3, 1.8 Hz), 1.91 (ddd, 1H, J=13.4, 10.4, 5.5 Hz); $^{13}$C NMR (100 MHz, CD$_3$OD) δ 161.79, 160.15, 123.82, 115.38, 113.88, 106.93, 69.80, 62.66, 61.11, 53.78, 41.12, 26.88; MS m/z: 343 (M+H$^+$), 93 (100%); HRMS (FAB) calcd for C$_{12}$H$_{16}$BrN$_4$O$_3$ (M+H$^+$): 343.0406. found: 343.0412.

Example 2

Chemoinformatic Analysis (−)-Agelastatin A was analyzed for chemoinformatic properties and physical descriptors. Pharmocophore properties for (−)-Agelastatin were then placed into comparison with a pool of 95% of commercial drugs (>1712 different drug molecules). The initial structure was derived in Chem-Draw and optimized in ChemBio3D using GAMESS for optimization of the structure with both RHF/3-21G level of theory and PM6, R-closed shell, PCM solvent for semi-empirical optimization (M. W. Schmidt et al. *J. Comput. Chem.*, 1993, 14, 1347-1363; N. Mills, *J. Am. Chem. Soc.*, 2006, 128, 13649-13650). The root-mean-square-deviation (RMSD) difference between the two optimized structures was <0.05 Å. The later structure was imported into Schrödinger's Maestro module for chemical profiling with QikProp (2011 version), which is shown in Table 1. Additionally, a similarity comparison was conducted against the most common pharmaceutical drugs, screening for the top five drugs with the most similar physical descriptors. Such a comparison does not preclude a common activity, but does indicate the likelihood of drug-like ability for (−)-Agelastatin.

TABLE 1

| Principal Descriptors: | | (Range 95% of Drugs) | |
|---|---|---|---|
| Solute Molecular Weight | 341.164 | (130.0/725.0) | |
| Solute Dipole Moment (D) | 2.47 | (1.0/12.5) | |
| Solute Total SASA | 482.208 | (300.0/1000.0) | |
| Solute Hydrophobic SASA | 137.23 | (0.0/750.0) | |
| Solute Hydrophilic SASA | 182.701 | (7.0/330.0) | |
| Solute Carbon Pi SASA | 96.563 | (0.0/450.0) | |
| Solute Weakly Polar SASA | 65.713 | (0.0/175.0) | |
| Solute Molecular Volume (Å$^3$) | 841.844 | (500.0/2000.0) | |
| Solute vdW Polar SA (PSA) | 112.601 | (7.0/200.0) | |
| Solute No. of Rotatable Bonds | 1 | (0.0/15.0) | |
| Solute as Donor-Hydrogen Bonds | 3 | (0.0/6.0) | |
| Solute as Acceptor-Hydrogen Bonds | 5.25 | (2.0/20.0) | |
| Solute Globularity (Sphere = 1) | 0.894 | (0.75/0.95) | |
| Solute Ionization Potential (eV) | 9.47 | (7.9/10.5) | |
| Solute Electron Affinity (eV) | 0.668 | (−0.9/1.7) | |
| Predictions for Properties: | | (Range 95% of Drugs) | |
| QP Polarizability (Angstroms$^3$) | 27.817M | (13.0/70.0) | |
| QP log P for hexadecane/gas | 9.301M | (4.0/18.0) | |
| QP log P for octanol/gas | 16.801M | (8.0/35.0) | |
| QP log P for water/gas | 12.147M | (4.0/45.0) | |
| QP log P for octanol/water | 1.267 | (−2.0/6.5) | |
| QP log S for aqueous solubility | −3.41 | (−6.5/0.5) | |
| QP log S-conformation independent | −4.494 | (−6.5/0.5) | |
| QP log K hsa Serum Protein Binding | −0.121 | (−1.5/1.5) | |
| QP log BB for brain/blood | −0.859 | (−3.0/1.2) | |
| No. of Primary Metabolites | 1 | (1.0/8.0) | |
| HERG K+ Channel Blockage: log IC50 | −3.705 | (concern below −5) | |
| Apparent Caco-2 Permeability (nm/sec) | 183 | (<25 poor, >500 great) | |
| Apparent MDCK Permeability (nm/sec) | 181 | (<25 poor, >500 great) | |
| QP log Kp for skin permeability | −4.451 | (Kp in cm/hr) | |
| Jm, max transdermal transport rate | 0.005 | (micrograms/cm$^2$-hr) | |
| Lipinski Rule of 5 Violations | 0 | (maximum is 4) | |
| Jorgensen Rule of 3 Violations | 0 | (maximum is 3) | |
| % Human Oral Absorption in GI (+−20%) | 75 | (<25% is poor) | |
| Qual. Model for Human Oral Absorption | HIGH | (>80% is high) | |
| 5 of 1712 molecules most similar to (—)-Agelastatin A | | | |
| Name | | Similarity (%) | |
| Clorexolone | | 88.3 | |
| Oxazepam | | 85.38 | |
| Lorazepam | | 84.55 | |
| Valdecoxib | | 83.23 | |
| Thalidomide | | 81.77 | |
| QP Breakdown (<for descriptor over training max) | | | |
| log Po/w | | −log S | |
| H-bond Donor | −0.9 | H-bond Donor | −1.205 |
| H-bond Acceptor | −2.557 | H-bond Acceptor | −2.749 |

TABLE 1-continued

| | | | |
|---|---|---|---|
| Volume | 5.492 | SASA | 9.138 |
| Ac x Dn^.5/SASA | 0.837 | Ac x Dn^.5/SASA | 1.885 |
| FISA | −1.264 | Rotor Bonds | −0.163 |
| Non-con amines | 0 | N Protonation | 0 |
| Non-con amides | 0 | Non-con amides | 0 |
| WPSA & PISA | 0.364 | WPSA | 0.286 |
| Constant | −0.705 | Constant | −3.783 |
| Total | 1.267 | Total | 3.41 | log BB

| | |
|---|---|
| Hydrophilic SASA | −1.523 |
| WPSA | 0.161 |
| Rotor Bonds | −0.06 |
| N Protonation | 0 |
| FOSA | 0 |
| Constant | 0.564 |
| Total | −0.859 |

$^a$ *An M indicates MW is outside training range.
Chemoinformatics reveals (−)-Agelastatin A has high probability of absorption via an oral route (FIG. 1, Table 1).
With a molecular weight of 341.2 Daltons and desirable range Chemoinformatics reveals (−)-Agelastatin A has a high probability of absorption via an oral route (FIG. 1, Table 1). With a molecular weight of 341.2 Daltons and a desirable range for surface accessible solvent area (SASA), number of rotatable bonds, number of hydrogen bond donors (HBD), number of hydrogen bond acceptors (HBA), permeability (log P), and solubility (log S), (−)-Agelastatin A is well within the desirable range of 95% of drugs. Lipinski's Rule of 5 and Jorgensen's Rule of 3 have zero violations when analyzing (−)-Agelastatin A (Table 1). Over a training set of 1712 orally available drugs, values were determined for the descriptors H-bond donors, H-bond acceptors, volume, SASA, hydrophilic component of SASA (FISA), protonation states, number of rotor bonds, weakly polar component of SASA (WPSA), and π component of SASA (PISA) plus the constant resulting in a log P and log S of 1.267 and −3.41, respectively. Additionally, log BB (blood-brain barrier) was determined from the descriptors hydrophilic SASA, WPSA, rotor bonds, N protonation, hydrophobic component of SASA (FOSA) plus the constant, yielding a total for log BB of −0.859. The apparent CACO permeability (predicted apparent Caco-2 cell permeability in nm/sec) and MDCK permeability (predicted apparent MDCK cell permeability in nm/sec) are 183 and 181, respectively. MDCK values >25 nm/sec are good indicators of moderate level of CNS penetration, since MDCK cells are considered to be a good mimic for the blood-brain barrier. Additionally, the predicted percent absorption in GI is approximately 75%. The top five drugs most similar to (−)-Agelastatin A in terms of chemoinformatic-physical descriptors are: Clorexolone (88.3%), Oxazepam (85.4%), Lorazepam (84.55%), Valdecoxib (83.2%), and Thalidomide (81.2%). Of these drugs, Lorazepam, Oxazepam, and Thalidomide exhibit good CNS penetration and may be used for their sedative, calming effect in CNS, while Valdecoxib is an anti-inflammatory drug (cyclooxygenase-2 selective inhibitor) and Clorexolone is a sulfonamide diuretic and antihypertensive.

As discussed above, the top five drugs most similar to AA in terms of physical descriptors are: Clorexolone (88.3%), Oxazepam (85.4%), Lorazepam (84.55%), Valdecoxib (83.2%), and Thalidomide (81.2%). While this does not indicate that AA has the same target, it does indicate with good likelihood that AA is a good drug candidate for crossing the blood-brain barrier. An MDCK value of 183 nm/sec was calculated, where a MDCK values >25 nm/sec is a good indicators of moderate CNS penetration, and correlates with the experimentally observed levels of BBB penetration (see Example 2). Along with the MDCK, log P, and log S measurements, the descriptors are within the criteria set by Hansch and Lipinski (A. Leo et al. *Chem Rev*, 1971, 71, 525-616; A. Lipinski et al. *Adv Drug Del Rev* 1997, 23, 3-25; and C. Hansch et al. *J. Am. Chem. Soc.*, 1963, 85, 2817).

Example 3

Agelastatin A (AA) in the Treatment of CNS Lymphoma

Agelastatin A (AA) suppresses proliferation and invasiveness of lymphoma cells. CNS PK analysis was performed on AA in a murine model. AA can cross the blood brain barrier with a CNS penetration rate of 10.09%. Pre-clinical therapeutic activity of AA in an orthotopic murine CNS lymphoma model shows that AA has a significant therapeutic activity against CNS lymphoma with prolongation of survival. AA decreases the intracerebral dissemination of lymphoma cells. The findings indicate that AA can cross the blood brain barrier and have a therapeutic impact on a brain tumor. Mechanistically, AA shows anti-osteopontin activity via transcriptional downregulation of osteopontin. It also downregulates NFkB signaling activity. AA has a therapeutic activity against CNS lymphoma. It can be used for other primary and secondary brain tumors.

Materials and Methods.

In Vitro Study

Reagents—

RPMI-1640 medium, OptiMEM, fetal bovine serum (FBS), Pencillin/Streptomycin/Amphotercin B (PSA), Dulbecco's Phosphate Buffered Saline (DPBS) were purchased from Mediatech (Manassas, Va.). Lipofectamine 2000, Trizol and PureLink RNA extraction kit were purchased from Invitrogen (Carlsbad, Calif.). Quantikine human osteopontin ELISA kit and human recombinant osteopontin were purchased from R&D Systems (Minneapolis, Minn.). Puromycin and molecular biology-grade reagents are from Sigma-Aldrich (St. Louis, Mo.). Rabbit anti-osteopontin was purchased from Rockland Immunochemicals (Gilbertsville, Pa.). Nano 6000 RNA analysis reagents (Agilent, Santa Clara, Calif.); PCR primers and Taqman FAST Universal PCR Master Mix (Applied Biosystems, Carlsbad, Calif.); BD Biocoat Matrigel Invasion Chamber (BD Biosciences, Sparks, Md.).

Cell Lines—

Raji cells were purchased from American Tissue Culture (Manassas, Va.). All cells were maintained in RPMI-1640 media with L-glutamine and supplemented with 20% (v/v) FBS and 1% (v/v) PSA. Raji cells infected with lentivirus constructs were grown in selection media containing 2.5 µg/ml puromycin. For experiments, unless specified otherwise, all cells were switched back to maintenance media.

Luciferase Transfection of Raji Lymphoma Cells—

The luciferase-expressing pSIN-luc vector was used to infect Raji cells. Producer cells (293 FT) were grown overnight at $4\times10^6$ cells per 10 cm plate in DMEM maintenance media containing 2-4 mM L-glutamine, 1 mM sodium pyruvate, 0.1 mM non-essential amino acids, 10% FBS. The next day cells were washed using DPBS, and 3 ml OptiMEM supplemented with 10% FBS was added to each plate. Three micrograms of pLenti plasmid was packaged with 9 µg ViraPower Packaging Mix in 1.5 ml OptiMEM, mixed with 36 µl LipofectAMINE 2000 (Invitrogen:Carlsbad, Calif.) and transfected into cells overnight at 37° C. in a humidified $CO_2$ incubator. Transfection media was replaced with DMEM maintenance media for 48 hours. Supernatant from pelleted 293 FT cells was collected, filtered, aliquoted and stored at −80° C.

For infection of Raji cells with lentivirus containing luciferase-expressing constructs, host cells were mixed 1:5 with virus and 7.5 µg/ml polybrene and gently centrifuged for 60 minutes at room temperature. Cells were resuspended and incubated overnight in a humidified $CO_2$ incubator. The next day cells were pelleted and resuspended in complete media to remove virus and polybrene particles. Luciferase expression was determined using Dual-Luciferase Reporter Assay System on a Veritas Microplate Luminometer (Promega Corp.: Madison, Wis.).

RNA Isolation and RT-PCR—

B lymphoma cells were grown at $1\times10^6$ cells in complete media. Cells were harvested by centrifugation, and total RNA was extracted by Trizol and PureLink kit as described by the manufacturer (Invitrogen: Carlsbad, Calif.). Residual genomic DNA contamination was removed by DNA-Free kit (Applied Biosystems: Carlsbad, Calif.). Total RNA was converted to cDNA using the High Capacity Reverse Transciption kit (Applied Biosystems: Carlsbad, Calif.) and diluted to 4 ng/µl RNA with nuclease-free water.

Real-time PCR was used to measure changes in osteopontin mRNA expression in lymphoma cells treated with DMSO or Agelastatin A. 20 ng of cDNA in 15 µl TaqMan FAST Universal PCR Master Mix containing PCR primers was assayed by real-time PCR on an AB 7900 FAST instrument (Applied Biosystems: Carlsbad, Calif.). $C_t$ values were determined by instrument software and relative osteopontin mRNA values were normalized to GAPDH. Significant difference of $C_t$ values was determined using a two-tailed Student's T-test.

Cell Proliferation Assay—

B lymphoma cells were seeded in triplicate at 50,000 cells per ml per well of a 24-well tissue culture plate in 0.5 ml of media. Cells were treated with vehicle control or Agelastatin A at 100, 500, or 1,000 nM. Cells were harvested and counted on the third day in a Coulter Particle Counter (Beckman-Coulter Corp.: Brea, Calif.). Two-tailed student T-test was used to analyze significant difference.

Invasion Assay—

Invasion assays were performed in triplicate using BD Biocoat Matrigel Invasion Chamber (BD Biosciences: Sparks, Md.) according to manufacturer's instructions (8-µm pore-size). Five percent serum was used as a chemoattractant in the bottom chamber. To test the impact of Agelastatin A (AA) on invasiveness of Raji cells, Raji cells were pre-treated for 1 hour with log dilutions of Agelastatin A in serum-free RPMI before transferring cells to the Matrigel chambers. Viability of Raji cells was ascertained by Trypan blue test after the treatment with AA. Statistical analysis was performed using two-tailed Student's T-Test.

ELISA—

$10^5$ Raji lymphoma cells were seeded in 5 ml media in 6-well plates in triplicate and were grown for four days. Cells were pelleted and the media was collected for analysis. Duplicate four hundred microliters of media supernatant were assayed for osteopontin by ELISA using Quantikine human osteopontin ELISA kit (R&D Systems, Inc., Minneapolis, Minn.). Statistical analysis was performed using two-tailed Student's T-Test.

Ex-Vivo Study

Ex-Vivo Brain Slice Assay—

The impact of Agelastatin A on the brain invasiveness of Raji B lymphoma cells was assessed ex vivo using a modified murine brain slice invasion assay. Briefly, these cells were first pre-transfected with luciferase (SP-DiI; Molecular Probes) just prior to invasion assays. Slice cultures of whole brains were produced from C57 mice. Two-month-old male C57BL/6J mice were sacrificed by $CO_2$ inhalation. Mice brains were removed, placed into sterile ice-cold PBS, and then coronally sectioned with a 1 mm coronal brain matrix into 1 mm slices at +2.00 to −1.00 bregma. Brain slices were placed aseptically onto transwell (8 µm pore size) membranes in six-well dishes. Culture media (DMEM, 10% FCS, 6.5 µg/ml glucose, 100 U/ml penicillin, 100 µg/ml streptomycin, and 2.5 µg/ml amphotericin B) was added into each well to a point just below that which would cover the brain slice. 25,000 Raji cells treated with DMSO or Agelastatin A 100 nM were deposited onto caudate putamen of brain slices, after ascertaining their viability by Trypan blue test. Cells were allowed to attach to the brain surface for one hour before the media was adjusted to just cover the surface of the slice. After 5 days incubation, the extent of lymphoma cell invasion into the brain slice was quantitated by bioluminesence imaging (BLI) in both slice and media. Brain slices were fixed in 4% paraformaldehyde for CD20 staining to identify Raji cells, which had invaded the brain slices.

Immunohistochemistry (IHC)—

Paraffin sections (10 µm thick) were fixed and mounted onto glass slides, blocked, and immunostained with antibody to CD20 to identify B lymphoma cells.

Determination of the Impact of Agelastatin a (AA) on Intracerebral Dissemination of Lymphoma Cells—

Murine brains harvested from the in-vivo experiments to assess the pre-clinical therapeutic activity of AA were studied by IHC. CD20-positive lymphoma cells were counted in the cerebral hemisphere contralateral to the tumor implantation side for dissemination in lateral, anterior, and posterior directions by ScanScope XT slide scanner and image analysis system (Aperio Spectrum, Vista, Calif.). One-way ANOVA was used to determine the statistical significance of the difference between the treated group and untreated control group.

In Vivo Study

Development of Murine CNS Lymphoma Model by Intracerebral Injection of Tumor Cells—

Athymic mice (nu/nu; 8-10 weeks old) were anesthetized with gasiform isofluorane and 25,000 Raji cells transfected with luciferase (as described in in vitro study) were stereotactically injected into the left cerebral hemisphere at coordinates (AP: 0.5 mm, LM: 2.5 mm, DV: 3 mm) from the bregma and skull at a volume of 5 µl and at a rate of 1 µl/min. The needle was left in place for 5 min after injection.

Bioluminescence Imaging of Mouse (BLI)—

BLI was conducted using a Xenogen Lumina optical imaging system (Caliper Life Sciences, Hopkinton, Mass.). Mice were anesthetized with isofluorane before intraperitoneal injections of luciferin at a dose of 150 mg/kg, providing a saturating substrate concentration for luciferase enzyme. Peak luminescent signals were recorded 10 minutes after luciferin injection. Regions of interest encompassing the intracranial area of signal were defined using Living Image software, and the total photons/s/steradian/cm$^2$ was recorded.

Central Nervous System (CNS) Pharmacokinetic Studies of Agelastatin A

Animals and Chemical—

The total of 90 male wild type C57BL/6J mice were used in this study. C57BL/6J mice were approximately 2 months of age and weighed 20~25 g. All mice were housed in a temperature-controlled room (23±12° C.) with a 12:12 light dark cycle (lights on at 0600). Purina 5001 Rodent Chow and tap water were available ad libitum at all times. Mouse use was approved by Mayo Foundation Institutional Animal Use and Care Committee (IACUC) and was consistent with NIH Guide for the Care and Use of Laboratory Animals. Agelastatin A was synthesized by Professor Takehiko Yoshimitsu at Graduate School of Pharmaceutical Sciences, Osaka University, Osaka, Japan. Professor Yoshimitsu has described details on the synthesis of this compound. Purity as determined by NMR spectra is >99%.

Microdialysis Surgery and Procedure—

A total of five mice were used in microdialysis experiments. On the day of surgery, mice were anesthetized with gasiform isoflurane (1% isoflurane in a mixture of 20% oxygen and 80% nitrogen gas) and immobilized in a stereotaxic frame (KOPF Instruments, Tujunga, Calif.). Anesthesia was maintained during the entire procedure. Each guide cannula (CMA Microdialysis Inc., Acton, Mass.) was stereotaxically implanted into the lateral ventricle (AP –0.2, L 1.0, V 2.0, relative to bregma and skull), and then secured to the skull by screws and dental cement. Following surgery, each mouse was housed individually with food and water ad libitum for 3-5 days for recovery from cannulation surgery. Microdialysis experiments were carried out on conscious, freely moving mice. On the day of the experiment, the stylet in the guide cannula was replaced with the microdialysis probe (CMA/7 with 2 mm membrane, CMA Microdialysis Inc., Acton, Mass.). The probe was perfused at 0.5 µl/min with artificial cerebrospinal fluid (146 mM NaCl, 1.2 mM CaCl2, 3 mM KCl, 1.0 mM MgCl2, 1.9 mM Na2HPO4, 0.1 mM NaH2PO4, pH 7.4). After at least 2 h equilibration, dialysate samples were automatically collected every 60 min into vials. Three baseline fractions were collected before saline injection (3 fractions) and then 24 samples were collected after Agelastatin A injection (2.5 mg/kg, intraperitoneal, i.p.). All samples were applied to the capillary electrophoresis with UV detection (CE-UV) for the determination of concentration of Agelastatin A in CSF. The position of the probe was verified by visual inspection at the end of each experiment.

Preparation of the Samples of Serum, Brain and Eye Tissue—

Total 85 mice were injected with 2.5 mg/kg Agelastatin A (intraperitoneal injection, i.p.). Every two hours, five mice were euthanized and the brain and eye tissues were harvested, homogenized in buffer (artificial CSF containing 10 mM EDTA) and centrifuged (10 min, 26,000×g, 4° C.). The supernatant was then applied to CE-UV. The blood was also collected at time points (10 min, 20 min, 30 min, 1 hr, 2 hr, 3 hr, 4 hr, 12 hr, 16 hr and 24 hr) from 5 mice for each time point, and centrifuged (10 min, 26,000×g, 4° C.). The serum was then applied to CE-UV.

Determination of Agelastatin A with the Use of CE-UV—

Agelastatin A in the microdialysate, serum, brain and eye tissues was measured by CE-UV (Agilent 3D CE). Briefly, the capillaries were preconditioned with 1 M sodium hydroxide for 2 min, water for 2 min and running buffer [100 mmol/l solution of ammonium acetate (adjusted to pH 3.1 with acetic acid)-acetonitrile (50:50, v/v)] for 3 min. The samples were injected at a pressure of 0.7 psi for 5 s and the injection volume was approximately 5 nl. After injection, the Agelastatin A was separated in a fused silica capillary of 50 µm I.D. and 50/65 cm length (effective length/total length) under 15 kv and 25° C. The absorbance from Agelastatin A was detected with UV at 280 nanomoles. Emission was collected on a photomultiplier tube (PMT). The detection limit of Agelastatin A is 1.6 picomoles. Statistical analysis was performed by two-way repeated measures ANOVA followed by Tukey's test was used. $P<0.05$ was considered significant. CNS penetration was determined as the ratio of CSF and blood area under the curve (AUC).

Pre-Clinical Evaluation of Agelastatin A in Raji Murine CNS Lymphoma Model—

Raji murine CNS lymphoma model was created as described in in vivo study section. After bioluminesence imaging (BLI) scanning on day 4 post intracerebral injection, animals were randomly assigned to four different groups. Control group (N=6) received vehicle IP every day for a total five days (Day 4~8 post tumor cell implantation). T1 group (N=8) received Agelastatin A 1.0 mg/Kg IP for four days. T2 group (N=8) received Agelastatin A 2.5 mg/Kg IP for four days. T3 group (N=8) received Agelastatin A 5 mg/kg IP every day for four days. BLI was used for real time monitoring of tumor growth. Differences in tumor growth were statistically analyzed by ANOVA. Kaplan-Meier analysis was used to analyze the therapeutic effect of Agelastatin A on survival.

Evaluation of the Impact of Agelastatin a on NFkB Signaling Pathway—

$10^5$ Raji cells were co-transfected overnight with a Cignal firefly luciferase-expressing NFkB reporter plasmid (NFkBr; SA Biosciences) together with a constitutively expressed Renilla luciferase reporter plasmid containing a CMV promoter. A promoterless vector (Neg-Luc) was co-transfected with the Renilla reporter for control. The next day, transfectants were treated with DMSO, 100 nM and 500 nM Agelastatin A for 48 hours followed by determination of NFkB activity. Data are presented as a ratio of firefly-to-Renilla luciferase luminescence.

An in-vivo experiment was also performed to assess impact of Agelastatin A on NFkB signaling in Raji cells implanted inside the murine brain. In serum free medium, Raji cells were transfected with NFkB reporter system. 25,000 cells were intracerebrally injected into athymic mice.

The mice were then treated with Agelastatin A at 2.5 mg/kg or 5 mg/kg intraperitoneally the next day. Bioluminescence imaging (BLI) of NFkB activity of intracerebral Raji lymphoma cells were measured on day 4 post intracerebral implantation.

Results

1) Agelastatin A Decreases Cell Proliferation and Brain-Invasiveness of Lymphoma Cells. (FIG. 1)

The cell proliferation assays showed that AA significantly suppressed proliferation of Raji lymphoma cells. It significantly decreased invasiveness of Raji cells in in-vitro invasion assay. Ex-vivo brain slice invasion assay showed that AA significantly decreased and disabled the brain invasiveness of Raji cells.

Figure 2A:
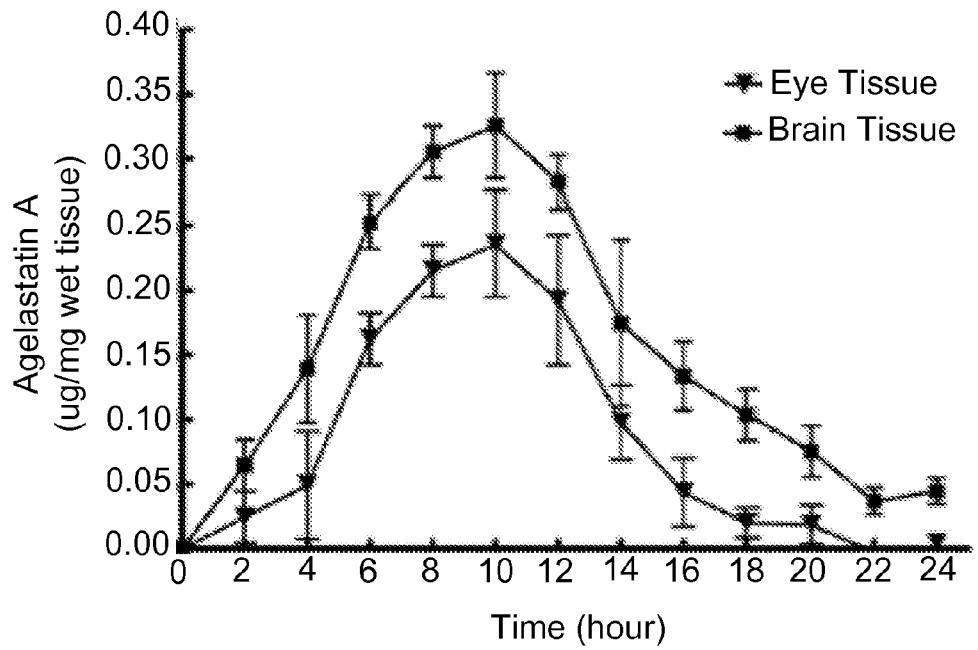
FIG. 2A shows that AA can penetrate the brain and eye tissue compartments.
Figure 2B:
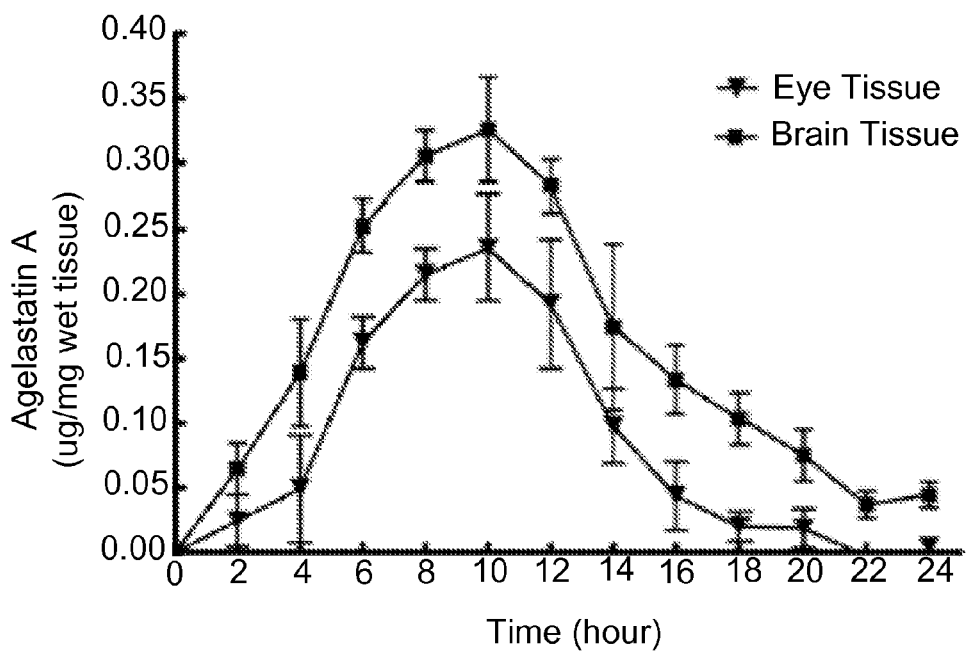
FIG. 2B shows that Agelastatin A has good CNS penetration. The area under the curve (AUC) for serum Agelastatin A levels was 33.8 and AUC for CSF Agelastatin A levels was 3.41. CNS penetration (CSF-to-serum AUC ratio) is 10.09%. Shown are means±SEMs for N=5.

2) Agelastatin A can Penetrate the Central Nervous System (FIG. 2)

The CNS PK analysis showed that AA could cross the blood brain barrier with CNS penetration rate of 10.09%. It was shown to penetrate into the brain and eye tissue compartments. As such, AA can penetrate into all the tissue compartments of the central nervous system including the brain, cerebrospinal fluid, and eyes. It is an important finding as a brain tumor like CNS lymphoma can involve all these tissue compartments of the central nervous system.

3) Agelastatin A has Significant Therapeutic Activity Against CNS Lymphoma with Prolongation of Survival. (FIG. 3)

Pre-clinical evaluation of AA in Raji orthotopic murine CNS lymphoma model showed that AA significantly decreased the tumor growth and significantly prolonged the survival. This proves the concept that AA can cross the blood brain barrier and have a therapeutic impact on the growth of a brain tumor with prolongation of survival.

4) Agelastatin A Decreases the Dissemination of Lymphoma Cells in the Brain (FIG. 4)

CNS lymphoma is a "whole brain" disease. To be therapeutically effective, any treatment must have an impact on 'whole brain" nature of CNS lymphoma. The results showed that AA significantly decreased dissemination of lymphoma cells in the brain, thus having an impact on the "whole brain" nature of CNS lymphoma. The findings show that AA can have an impact on the "whole brain" nature of brain tumors.

5) Agelastatin A Shows Anti-Osteopontin (OPN) Activity and Suppresses NFkB Signaling Activity (FIG. 5)

Mechanistically, the studies showed that AA significantly decreased secretion of osteopontin by lymphoma cells by transcriptionally downregulating osteopontin. OPN has been shown to promote various biological properties of cancer cells such as cell proliferation, invasiveness, metastasis, and angiogenesis. As such, anti-osteopontin activity is important for anti-cancer activity of AA. The studies also showed that AA significantly downregulated NFkB signaling, which plays an important role in many different cancers. The in vivo study shows that AA can cross the blood brain barrier and can impact the molecular signaling activity (NFkB signaling pathway) in a brain tumor.

Example 4

Cytotoxicity of AA and AA Analogues Against Cancer Cell Lines

AA and various AA analogues were tested for their in vitro cytotoxicity against three cancer cell lines: DU145 (prostate cancer cells), Raji B cells (Burkitt's lymphoma cells), and MB-468 (triple-negative breast cancer cells).

Materials and Methods

Raji cells and MB-468 cells were purchased from American Tissue Culture (Manassas, Va.). They were maintained in RPMI-1640 media with L-glutamine and supplemented with 10% (v/v) FBS and 1% (v/v) penicillin-streptomycin. Raji cells or MB-468 were seeded in triplicate at 50,000 cells per mL per well of a 24-well tissue culture plate in 0.5 mL of media. The next day, the cells were treated with vehicle control or a drug (AA or one of its 18 analogues) at 18.75, 37.5, 75, 150, 300, 600, 1200, 2400, 5000, or 10,000 nM. Cells were harvested and counted on the third day in a Coulter Particle Counter (Beckman-Coulter Corp.: Brea, Calif.). IC50 values were calculated using GraphPad Prism 5 (GraphPad Software Inc., La Jolla, Calif.).

Human DU145 prostate cancer cells were cultured in RPMI 1640 supplemented with heat-inactivated 10% FBS and kanamycin (50 µg/mL) in a humidified atmosphere of 5% $CO_2$ at 37° C. The cell suspension in the culture medium was plated into each well of 96-well plates (10,000 cells/well/100 µL). After 24 h, testing compounds were added, and then the plates were incubated for an additional 24 h in a humidified atmosphere of 5% $CO_2$ at 37° C. The cell proliferation was detected according to an established MTT method, as previously described (T. Mosmann, *J. Immunol. Methods* 1983, 65, 55). The $IC_{50}$ value was determined by linear interpolation from the growth inhibition curve.

Results

The results of this study are shown in Table 2.

TABLE 2

Cytotoxicities ($IC_{50}$ (µM)) of AA and AA analogues against cancer cell lines

| | | Cytotoxicity (IC50, µM) | | |
|---|---|---|---|---|
| | Compounds | DU145 | Raji | MB-468 |
| 1 | AA | 2.3 | 0.14 | 2.8 |
| 2 | DeAMDeBAA | ND | >10 | >10 |
| 3 | DeBUAA | ND | >10 | >10 |
| 5 | DeBAA | >10 | 3.16 | 3 |
| 6 | DeBEAA | >10 | ND | ND |
| 7 | CAA | 1.2 | 0.18 | 0.08 |
| 8 | CEAA | 2.6 | 0.3 | 0.28 |
| 9 | DCEAA | 1.4 | 0.62 | 0.44 |
| 10 | EAA | >10 | ND | ND |
| 14 | N-PMBAA | >10 | ND | ND |
| 15 | CPAA | 5 | 0.4 | 1 |
| 16 | PAA | 6 | 3.8 | 1.5 |
| 17 | APAA | >10 | ND | ND |
| 18 | UAA | ND | >10 | >10 |
| 19 | ent-AA | >10 | ND | ND |

(ND = not determined).

Example 5

CNS Pharmacokinetic Analysis of AA, CAA, CEAA, and DCEAA

Pharmacokinetic analysis of AA and the three analogues was performed in rats to determine their capacity to penetrate the central nervous system. Specifically, the three Agelastatin A (AA) analogues are Chloroagelastatin A (CAA), Chloroethylagelastatin A (CEAA), and Dichloroethylagelastatin A (DCEAA).

Materials and Methods
Animals and Housing

Male Sprague-Dawley rats (Harlan, Indianapolis, Ind., USA) were used in this CNS pharmacokinetic study on Agelastatin A and its three analogues (CAA, CEAA, and DCEAA). Six rats were used for each drug. The rats were approximately 2 months old and weighed 300±25 g at the beginning of the study. All rats were housed in a temperature-controlled room (23±2° C.) with a 12:12 light dark cycle (lights off at 6:00 pm). Purina 5001 Rodent Chow and tap water were available ad libitum at all times.

Microdialysis Surgery and Procedure

Rats were anesthetized with gasiform isoflurane (1% isoflurane in a mixture of 20% oxygen and 80% nitrogen gas) and immobilized in a stereotaxic frame (KOPF Instruments, Tujunga, Calif.). Anesthesia was maintained during the entire procedure. The guide cannula (CMA Microdialysis Inc., Acton, Mass.) was stereotactically implanted into the lateral ventricle (AP −0.9, L 1.6, V 3.4, relative to bregma and skull), and then secured to the skull by screws and dental cement. Following surgery, each rat was housed individually with food and water ad libitum for 3 days for recovery from cannulation surgery. Microdialysis experiments were carried out on conscious, freely moving rats. On the day of the experiment, the stylet in the guide cannula was replaced with the microdialysis probe (CMA/11 with 4 mm membrane, CMA Microdialysis Inc., Acton, Mass.) and a vascular microdialysis probe (CMA/20 with 4 mm membrane, CMA Microdialysis Inc, Acton, Mass.)) was implanted into a jugular vein. The probes had inlet tubes connected to syringes to deliver artificial cerebrospinal fluid (146 mM NaCl, 1.2 mM $CaCl_2$, 3 mM KCl, 1 mM $MgCl_2$, 1.9 mM $Na_2HPO_4$, 0.1 mM $NaH_2PO_4$, pH 7.4) into the ventricle and Dulbecco's phosphate-buffered saline (D-PBS) into the blood at 0.5 µl/min flow rate. The outlet tubes were connected to a microfraction collector and the dialysates were collected at 4° C. Rats were allowed to recover for at least 24 hours prior to the administration of drugs. Single 2.5 mg/kg dose administered intravenously was used for all the drugs. Three baseline fractions were collected before the drug injection and then 22 samples were collected over 18 hours after the injection. All samples were applied to the capillary electrophoresis with UV detection (CE-UV) for the determination of concentration of the drug in CSF and blood. The rats were sacrificed using $CO_2$ inhalation after the experiment. The position of the probe was verified by visual inspection at the end of each experiment.

Determination of Agelastatin A and its Three Analogues with the Use of CE-UV

The drug concentration in the microdialysate was measured by CE-UV (Agilent 3D CE). Briefly, the capillaries were preconditioned with 1 M sodium hydroxide for 2 min, water for 2 min and running buffer [100 mmol/L solution of ammonium acetate (adjusted to pH 3.1 with acetic acid)-acetonitrile (50:50, v/v)] for 3 min. The samples were injected at a pressure of 0.7 psi for 5 s and the injection volume was approximately 5 nl. After injection, the drug was separated in a fused silica capillary of 50 µm I.D. and 50/65 cm length (effective length/total length) under 15 kv and 25° C. The absorbance from the drug was detected with UV at 280 nm. The emission was collected on a photomultiplier tube (PMT). The detection limit of AA, CAA, CEAA and DCEAA was 3.8 nM, 1.9 nM, 1.2 nM and 2.9 nM, respectively.

Statistical Analysis

Two-way repeated measures ANOVA followed by Tukey's test was used. $P<0.05$ was considered significant. CNS penetration is determined as the ratio of CSF and blood area under the curve (AUC).

Results

The three analogues have improved CNS penetration—CAA (16%), CEAA (27%), and DCEAA (30.7%) compared to AA (6.4%) (FIG. 6). The correlative analysis between the structure of the three analogues and their improved CNS penetration compared to AA indicated the importance of certain structural modifications in enhancing CNS penetration. The findings suggest that the attachment of the ethyl substituent onto the $N_1$ position and the chlorine atom(s) on the pyrrole ring likely provides the appropriate hydrophobicity, allowing for better CNS penetration. In addition, all three analogues achieved the peak CSF concentrations, which were significantly higher than their $IC_{50}$ values for glioblastoma cells, breast cancer cells and lymphoma cells (FIG. 6). Such a finding indicates that these compounds are likely candidates for brain cancer therapeutics.

Example 6

Preclinical Evaluation of AA Analogues for In-Vitro Cytotoxicity Against Cancer Cell Lines In-vitro assays were performed to assess the cytotoxic impact of AA analogues on breast cancer cell lines (MB-468, MB-453, and T47D), lymphoma cell lines (Raji and OCI-LY10), and glioblastoma multiforme cell line (U87). The three breast cancer cell lines represent three subtypes of breast cancer: triple-negative (MB-468), Her2-positive (MB-453), and hormone receptor positive (T47D).

Materials and Methods $IC_{50}$ values of Agelastatin A and three analogues (CAA, CEAA, and DCEAA) were determined using on cell proliferation assay. The $IC_{50}$ values obtained for each compound represents the concentration of the tested compound that is needed to decrease the cancer cell count by 50%. Cancer cells were seeded in triplicate at 50,000 cells per well of a 24-well plate in 0.5 ml medium. The next day, cells were treated with Agelastatin A and its analogues at doses of 0, 18.75 nM, 37.5 nM, 75 nM, 150 nM, 300 nM, 600 nM, 1.2 µM, 2.4 µM, 5 µM and 10 µM. Cells were harvested and counted on the sixth day using a Beckman Coulter counter. The $IC_{50}$ was determined by nonlinear regression analysis using GraphPad Prism 5 (GraphPad Software Inc., La Jolla, Calif.).

Results

Results are shown in Table 3. AA analogues were found to be comparable to or more potent than AA. For all the cancer cell lines tested, $IC_{50}$ values for the analogues were mostly in low nanomolar concentrations. For breast cancer cell lines, the three analogues were more potent than AA for triple-negative breast cancer (MB-468) and Her2-positive breast cancer (MB-453), and comparable results are seen for hormone-receptor positive breast cancer (T47D). For glioblastoma multiforme (U87), the three analogues were all more potent than AA. For lymphoma, the results were found to be comparable amongst the compounds.

TABLE 3

Cytotoxicities [IC$_{50}$] of AA and AA analogues against cancer cell lines.

| Compounds | Breast Cancer cell lines | | | GBM | Lymphoma | |
| --- | --- | --- | --- | --- | --- | --- |
| | IC$_{50}$ (MB-468) | IC$_{50}$ (MB-453) | IC$_{50}$ (T47D) | IC$_{50}$ (U87) | IC$_{50}$ (Raji) | IC$_{50}$ (OCI-LY10) |
| AA    | 2.8 µM    | 643.9 nM | 55.12 nM  | 2.8 µM    | 136.6 nM | 162.3 nM |
| CAA   | 81.13 nM  | 91.9 nM  | 29.77 nM  | 96.6 nM   | 180.8 nM | 101.6 nM |
| CEAA  | 276.8 nM  | 141.4 nM | 20.70 nM  | 109 nM    | 295.9 nM | 119.3 nM |
| DCEAA | 443.7 nM  | 104.2 nM | 101.1 nM  | 255.8 nM  | 619 nM   | 429.2 nM |

Example 7

Preclinical Evaluation of AA Analogues for Therapeutic Efficacy Against Brain Tumors in Murine Models Therapeutic efficacy of AA analogues against brain tumors was evaluated in murine models.
Materials and Methods
Animal and Housing Female athymic mice (8-10 weeks old and weighing 20-25 g at the beginning of the study) were purchased from Harlan laboratories (Indianapolis, Ind.). They were housed in a temperature-controlled sterilized room (23±2° C.) with a 12-h light/dark cycle and free access to food and water throughout the study.
Murine Orthotopic Brain Tumor Models Murine brain tumor models were created by intracerebral injection of luciferase-transfected cancer cells in athymic mice under anesthesia using a stereotactic platform. For murine model for CNS lymphoma, $1 \times 10^5$ OCI-LY10 B lymphoma cells were used. For murine model for metastatic breast cancer of the brain (MBCB), $1 \times 10^5$ MB-468 triple-negative breast cancer cells were used. For murine model for glioblastoma multiforme (GBM), $1.75 \times 10^5$ U87 cells were used. Eight-week-old athymic mice underwent a minimum 7-day acclimation/quarantine prior to surgery. Surgery was performed in a laminar flow hood under sterile conditions. Tylenol 300 mg/kg PO was given for analgesia 48 hours before the surgery and continuing 48 hours postoperatively. Anesthesia was achieved by inhalation of 1-2% isoflurane. After the mouse became well anesthetized, it was placed in the Kopf stereotactic instrument. A small amount of BNP antibiotic cream (a mixture of Bacitracin, Neomycin and Polymyxin) was smeared on its eyes to prevent infection and corneal damage during surgery. A strip of soft fabric was placed over the mouse's body and tail to prevent excessive heat loss during surgery. The scalp area was cleaned with a 2% solution of Betadine and dried with cotton tipped applicator. A midline sagittal incision was made in the scalp. A small burr hole was drilled in the left skull with a surgical drill (Kopf) or a Dremel drill according to the coordinates (AP: 0.5 mm, LM: 2.5 mm) as determined by reference to the mouse brain atlas by Franklin and Paxinos. The dura mater was surgically exposed, and a 10 µl Hamilton syringe with a 26S-gauge beveled needle was lowered into the left cerebral hemisphere up to a depth of 3 mm and 5 µl of tumor cells were slowly infused (0.5 µl/min). The needle was left in place for 5 minutes to prevent reflux and then was slowly removed. The skin was closed with wound clips. The mice recovered from anesthesia and surgery in a warm environment and were not returned to their cages until motor activity returned. Cages were placed on top of a heating pad to minimize the loss of body heat during the recovery. The mice were monitored post-operatively at least twice a day for 5 days or until recovery was complete.
Bioluminescence Imaging of Mouse (BLI)

BLI was used to assess the impact of the treatments on the brain tumor growth. After intracerebral injection of cancer cells, all the mice were subjected to bioluminesence imaging (BLI) twice a week starting at day-4 post-intracerebral injection to monitor the real-time in vivo tumor growth. BLI was conducted using a Xenogen Lumina optical imaging system (Caliper Life Sciences, Hopkinton, Mass.). Mice were anesthetized with isofluorane before intraperitoneal injections of luciferin at a dose of 150 mg/kg, providing a saturating substrate concentration for luciferase enzyme. Peak luminescent signals were recorded 10 minutes after luciferin injection. Regions of interest encompassing the intracranial area of signal were defined using Living Image software (Xenogen, Alameda, Calif.), and the total photons/s/steradian/cm2 was recorded.
In Vivo Preclinical Evaluation of AA, CAA, CEAA, and DCEAA in Murine Orthotopic Brain Tumor Models Five mice each were assigned to one of seven treatment groups or one vehicle control group for all three brain tumor models. Mice in experimental groups received either 2.5 mg/kg or 5 mg/kg of AA, CEAA, or DCEAA by intraperitoneal route daily for 4 days. For CAA, only 2.5 mg/Kg by intraperitoneal route daily for 4 days was used. The control group received DMSO by intraperitoneal route for 4 days. The end point for the survival analysis was the development of limb paralysis. Animals were checked at least twice per day. Animals that reached the end point were sacrificed by $CO_2$ anesthesia. Real time tumor growth was monitored by BLI. Tumor growth as determined by BLI and survival data were analysed for statistical difference between the groups.
Statistical Analysis One-way ANOVA was used to compare the difference between the groups at each time point. Two-way repeated measures ANOVA was used to analyse the interaction between the time and treatment. Survival analysis was performed by Kaplan Meier method. Kaplan Meier survival curves were generated using Prism5 software and the statistical difference between curves was derived with a log-rank test. P<0.05 was considered significant.
Results
OCI-LY10 Orthotopic Murine CNS Lymphoma Model As shown in FIG. 7, AA, CAA, CEAA, and DCEAA significantly decreased tumor growth and significantly prolonged survival in all treatment groups compared to the control group. Better tumor growth control and survival were seen with CEAA and DCEAA treatment groups compared to AA treatment group at both 2.5 mg/kg and 5 mg/kg dose levels. For CEAA and DCEAA, 5 mg/kg groups achieved better survival than 2.5 mg/kg groups. CEAA and DCEAA were well tolerated at both dose levels. Some weight loss was seen with AA at 5 mg/kg dose level and CAA at 2.5 mg/kg.

MB-468 Orthotopic Murine Model for Metastatic Breast Cancer of the Brain

As shown in FIG. 8, AA, CAA, CEAA, and DCEAA significantly decreased tumor growth and significantly prolonged survival in all treatment groups compared to the control group. CAA at 2.5 mg/kg dose level and DCEAA at 5 mg/kg dose level exhibited the best survival outcome. At 5 mg/kg dose level, DCEAA and CEAA groups had better survival than the AA group. For AA, CEAA, and DCEAA, 5 mg/kg groups had better survival than 2.5 mg/kg groups. CEAA and DCEAA were well tolerated at both dose levels. Some weight loss was seen with AA at 5 mg/kg dose level and CAA at 2.5 mg/kg.

U87 Orthotopic Murine Model for Glioblastoma Multiforme

As shown in FIG. 9, AA, CAA, CEAA, and DCEAA significantly decreased tumor growth and significantly prolonged survival in all treatment groups compared to the control group. At 2.5 mg/kg dose level, no significant differences were seen between the treatment groups. At 5 mg/kg dose level, DCEAA achieved better survival than AA and CEAA. For AA, CEAA, and DCEAA, 5 mg/kg groups achieved better tumor growth control and survival compared to 2.5 mg/kg groups. CEAA and DCEAA were well tolerated at both dose levels. Some weight loss was seen with AA at 5 mg/kg dose level and CAA at 2.5 mg/kg.

Results for the above experiments are further detailed in Table 4.

TABLE 4

Median survival for preclinical evaluation of AA and its analogues in the CNS lymphoma, metastatic breast cancer of the brain and glioblastoma multiforme models.

| Drugs | CNS Lymphoma (OCI-LY10) | P value (vs control) | Breast Cancer (MB-468) | P value (vs control) | GBM (U-87) | P value (vs control) |
|---|---|---|---|---|---|---|
| Control | 35 | — | 52 | — | 25.5 | — |
| AA 2.5 mg/kg | 48.5 | 0.0101 | 57 | 0.0204 | 28 | 0.0389 |
| AA 5 mg/kg | 46 | 0.0216 | 60.5 | 0.0007 | 30 | 0.0177 |
| CEAA 2.5 mg/kg | 57 | 0.0042 | 56 | 0.0029 | 29 | 0.0389 |
| CEAA 5 mg/kg | 65 | 0.0008 | 64 | 0.0002 | 31 | 0.0177 |
| DCEAA 2.5 mg/kg | 60 | 0.0042 | 61 | 0.0053 | 30 | 0.0389 |
| DCEAA 5 mg/kg | 69 | 0.0101 | 75 | 0.0026 | 34 | 0.0389 |
| CAA 2.5 mg/kg | 49 | 0.0042 | 75 | 0.0053 | 31 | 0.0389 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula I:

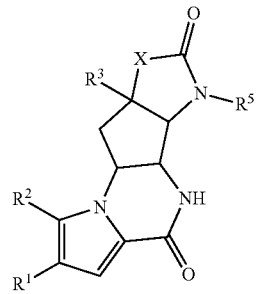

or a pharmaceutically acceptable salt thereof, wherein:

$X$ is selected from the group consisting of O and $NR^4$;

$R^1$ is selected from the group consisting of H and Cl;

$R^2$ is selected from the group consisting of H, F, Cl, Br, I, $C_{1-6}$ alkyl, cycloalkyl, aryl, heterocycloalkyl and heteroaryl, wherein each $C_{1-6}$ alkyl, cycloalkyl, aryl, heterocycloalkyl and heteroaryl is optionally and independently substituted with one or more substituents selected from the group consisting of halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl), aryl, fluoroalkyl, nitroalkyl, —$NO_2$, —CN, —N($R_9$)—C(O)—($C_1$-$C_{10}$ alkyl), —C(O)—($C_1$-$C_{10}$ alkyl), $C_2$-$C_{10}$ alkylthioalkyl, —C(O)—O—($C_1$-$C_{10}$ alkyl), —OH, —$S(O)_2$, =S, —C(O)—OH, —$N(R^9)_2$, —C(O)—($C_1$-$C_{10}$ alkyl)-$CF_3$, —C(O)—$CF_3$, —($C_1$-$C_{10}$ aryl)-S—($C_6$-$C_{10}$ aryl), —C(O)—($C_6$-$C_{10}$ aryl), —$(CH_2)_m$—O—$(CH_2)_m$—O—($C_1$-$C_{10}$ alkyl), —C(O)—$N(R^9)_2$, —C(S)—$N(R^9)_2$, —$S(O)_2$—$N(R^9)_2$, —$N(R^9)$—C(O)—$N(R^9)_2$ and —$N(R^9)$—C(S)—$N(R^9)_2$, wherein each m is independently 1, 2, 3, 4, 5, 6, 7 or 8;

$R^3$ is selected from the group consisting of H and OH;

$R^4$ is $C_{1-6}$ alkyl, optionally substituted with one or more substituents selected from the group consisting of halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl), aryl, fluoroalkyl, nitroalkyl, —$NO_2$, —CN, —N($R_9$)—C(O)—($C_1$-$C_{10}$ alkyl), —C(O)—($C_1$-$C_{10}$ alkyl), $C_2$-$C_{10}$ alkylthioalkyl, —C(O)—O—($C_1$-$C_{10}$ alkyl), —OH, —$S(O)_2$, =S, —C(O)—OH, —$N(R^9)_2$, —C(O)—($C_1$-$C_{10}$ alkyl)-$CF_3$, —C(O)—$CF_3$, —($C_1$-$C_{10}$ aryl)-S—($C_6$-$C_{10}$ aryl), —C(O)—($C_6$-$C_{10}$ aryl), —$(CH_2)_m$—O—$(CH_2)_m$—O—($C_1$-$C_{10}$ alkyl), —C(O)—$N(R^9)_2$, —C(S)—$N(R^9)_2$, —$S(O)_2$—$N(R^9)_2$, —$N(R^9)$—C(O)—$N(R^9)_2$ and —$N(R^9)$—C(S)—$N(R^9)_2$, wherein each m is independently 1, 2, 3, 4, 5, 6, 7 or 8;

$R^5$ is selected from the group consisting of H and $C_{1-6}$ alkyl, wherein $C_{1-6}$ alkyl is optionally substituted with one or more substituents selected from the group consisting of halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl), fluoroalkyl, nitroalkyl, —$NO_2$, —CN, —N($R_9$)—C(O)—($C_1$-$C_{10}$ alkyl), —C(O)—($C_1$-$C_{10}$ alkyl), $C_2$-$C_{10}$ alkylthioalkyl, —C(O)—O—($C_1$-$C_{10}$ alkyl), —OH, —$S(O)_2$, =S, —C(O)—OH, —$N(R^9)_2$, —C(O)—($C_1$-$C_{10}$ alkyl)-$CF_3$, —C(O)—$CF_3$, —($C_1$-$C_{10}$ aryl)-S—($C_6$-$C_{10}$ aryl), —C(O)—($C_6$-$C_{10}$ aryl), —$(CH_2)_m$—O—$(CH_2)_m$—O—($C_1$-$C_{10}$ alkyl), —C(O)—$N(R^9)_2$, —C(S)—$N(R^9)_2$, —$S(O)_2$—$N(R^9)_2$ —$N(R^9)$—C(O)—$N(R^9)_2$ and —$N(R^9)$—C(S)—$N(R^9)_2$, wherein each m is independently 1, 2, 3, 4, 5, 6, 7 or 8; and each $R^9$ is independently selected from the group consisting of H, alkyl, cycloalkyl, aryl and alkylaryl;

with the proviso that:
(i) if $R^1$ is H, $R^2$ is Br, $R^3$ is OH and $R^5$ is H, then $R^4$ is not $CH_3$;
(ii) if $R^1$ is H, $R^2$ is H, $R^3$ is OH and $R^5$ is H, then $R^4$ is not $CH_3$;
(iii) if $R^1$ is H, $R^2$ is H, $R^3$ is H and $R^5$ is H, then X is not O; and
(iv) the compound of formula (I) is not

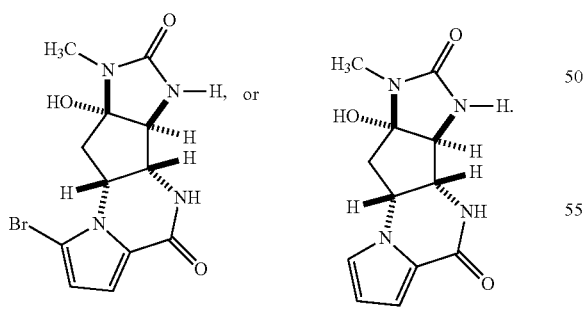

2. The compound of claim 1, wherein X is $NR^4$.
3. The compound of claim 2, wherein $R^4$ is $CH_2CH_3$.
4. The compound of claim 1, wherein $R^2$ is selected from the group consisting of H and Cl.
5. The compound of claim 1, wherein $R^3$ is OH.
6. The compound of claim 1, wherein the compound is selected from the group consisting of:

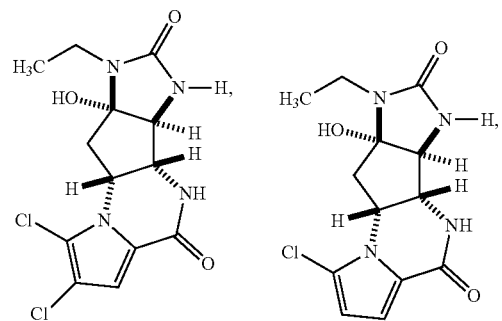

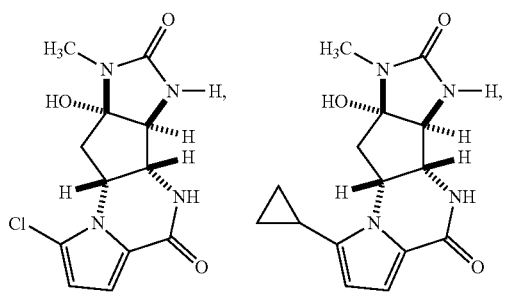

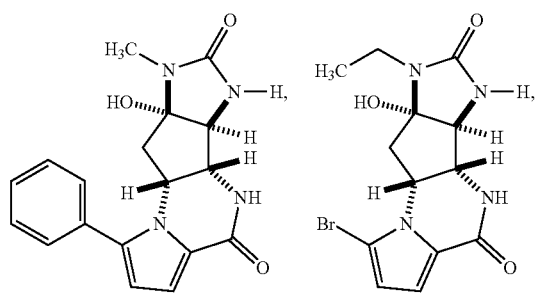

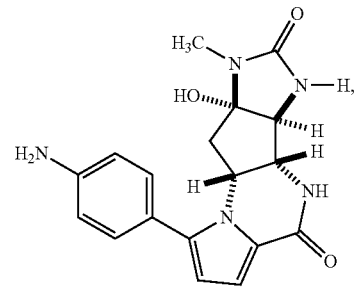

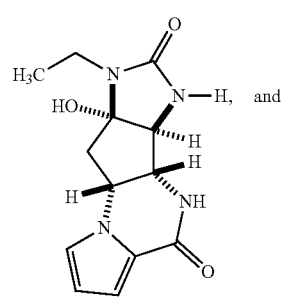

-continued

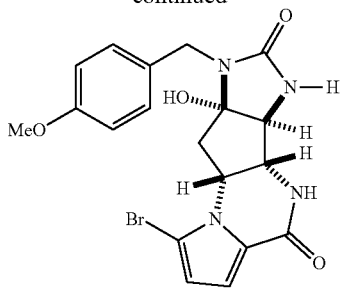

or a pharmaceutically acceptable salt thereof.

7. The compound of claim 1, wherein the compound is selected from the group consisting of:

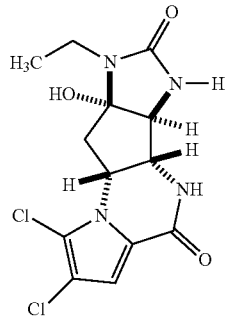 and 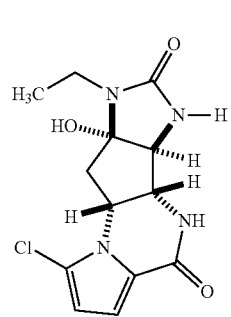

or a pharmaceutically acceptable salt thereof.

8. A pharmaceutical composition comprising a compound of claim 1, or a pharmaceutically acceptable salt thereof, and a pharmaceutically acceptable carrier.

9. A method for treating a primary or secondary brain tumor in a patient in need thereof, said method comprising administering to the patient a therapeutically effective amount of a compound of formula I:

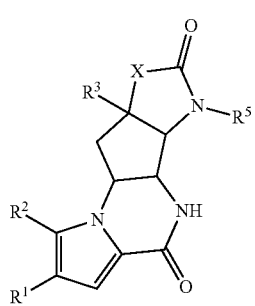

or a pharmaceutically acceptable salt thereof,
wherein:
X is selected from the group consisting of O and $NR^4$;
$R^1$ and $R^2$ are independently selected from the group consisting of H, F, Cl, Br, I, $C_{1-6}$ alkyl, cycloalkyl, aryl, heterocycloalkyl and heteroaryl, wherein each $C_{1-6}$ alkyl, cycloalkyl, aryl, heterocycloalkyl and heteroaryl is optionally and independently substituted with one or more substituents selected from the group consisting of halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, toluoyl, xylenyl, biphe- nyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—$(C_1$-$C_{10}$ alkyl), —$NO_2$, —CN, —$N(R_9)$—C(O)—$(C_1$-$C_{10}$ alkyl), —C(O)—$(C_1$-$C_{10}$ alkyl), $C_2$-$C_{10}$ alkylthioalkyl, —C(O)—O—$(C_1$-$C_{10}$ alkyl), —OH, —S(O)$_2$, =S, —C(O)—OH, —$N(R^9)_2$, —C(O)—$(C_1$-$C_{10}$ alkyl)-CF$_3$, —C(O)—CF$_3$, —$(C_1$-$C_{10}$ aryl)-S—$(C_6$-$C_{10}$ aryl), —C(O)—$(C_6$-$C_{10}$ aryl), —$(CH_2)_m$—O—$(CH_2)_m$—O—$(C_1$-$C_{10}$ alkyl), —C(O)—$N(R^9)_2$, —C(S)—$N(R^9)_2$, —S(O)$_2$—$N(R^9)_2$, —$N(R^9)$—C(O)—$N(R^9)_2$ and —$N(R^9)$—C(S)—$N(R^9)_2$, wherein each m is independently 1, 2, 3, 4, 5, 6, 7 or 8;
$R^3$ is selected from the group consisting of H, OH and $OC_{1-6}$ alkyl;
$R^4$ and $R^5$ are independently selected from the group consisting of H and $C_{1-6}$ alkyl, wherein $C_{1-6}$ alkyl is optionally substituted with one or more substituents selected from the group consisting of halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, toluoyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—$(C_1$-$C_{10}$ alkyl), aryl, fluoroalkyl, nitroalkyl, —$NO_2$, —CN, —$N(R_9)$—C(O)—$(C_1$-$C_{10}$ alkyl), —C(O)—$(C_1$-$C_{10}$ alkyl), $C_2$-$C_{10}$ alkylthioalkyl, —C(O)—O—$(C_1$-$C_{10}$ alkyl), —OH, —S(O)$_2$, =S, —C(O)—OH, —$N(R^9)_2$, —C(O)—$(C_1$-$C_{10}$ alkyl)-CF$_3$, —C(O)—CF$_3$, —$(C_1$-$C_{10}$ aryl)-S—$(C_6$-$C_{10}$ aryl), —C(O)—$(C_6$-$C_{10}$ aryl), —$(CH_2)_m$—O—$(CH_2)_m$—O—$(C_1$-$C_{10}$ alkyl), —C(O)—$N(R^9)_2$, —C(S)—$N(R^9)_2$, —S(O)$_2$—$N(R^9)_2$, —$N(R^9)$—C(O)—$N(R^9)_2$ and —$N(R^9)$—C(S)—$N(R^9)_2$, wherein each m is independently 1, 2, 3, 4, 5, 6, 7 or 8; and
each $R^9$ is independently selected from the group consisting of H, alkyl, aryl and alkylaryl;
with the proviso that:
(i) if $R^1$ is H, $R^2$ is Br, $R^3$ is OH and $R^5$ is H, then $R^4$ is not $CH_3$.

10. The method of claim 9, wherein the compound is selected from the group consisting of:

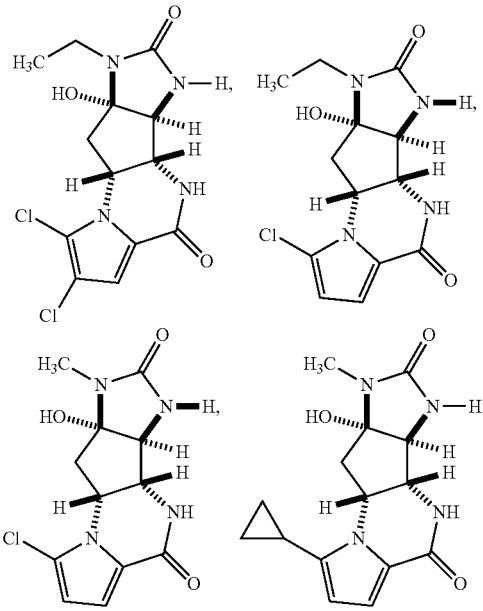

-continued
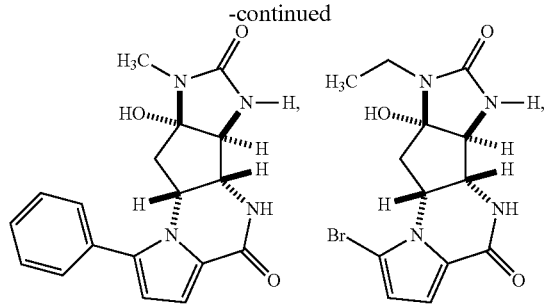
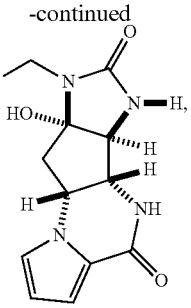
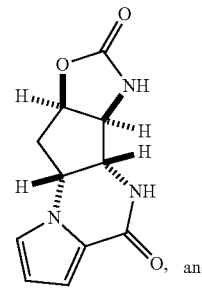
-continued
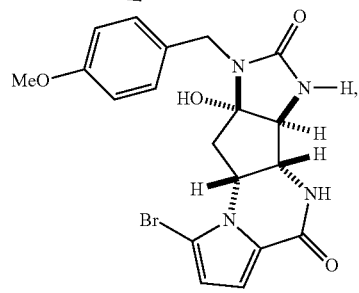
or a pharmaceutically acceptable salt thereof.
* * * * *